US008452653B1

(12) United States Patent
Gottfurcht et al.

(10) Patent No.: US 8,452,653 B1
(45) Date of Patent: May 28, 2013

(54) METHOD FOR PROVIDING INFORMATION AND RECOMMENDATIONS BASED ON USER ACTIVITY

(75) Inventors: Elliot A. Gottfurcht, Pacific Palisades, CA (US); Grant E. Gottfurcht, Pacific Palisades, CA (US); Shawn C. Dunn, Los Angeles, CA (US)

(73) Assignee: Personal Data Network Corporation, Pacific Palisades, CA (US)

( * ) Notice: Subject to any disclaimer, the term of this patent is extended or adjusted under 35 U.S.C. 154(b) by 2419 days.

(21) Appl. No.: 10/611,097

(22) Filed: Jun. 30, 2003

Related U.S. Application Data

(62) Division of application No. 09/525,235, filed on Mar. 15, 2000, now Pat. No. 6,611,881.

(51) Int. Cl.
*G06Q 30/00* (2012.01)

(52) U.S. Cl.
USPC .................. 705/14.25; 705/14.23; 705/14.36; 705/14.38; 705/14.49; 705/14.51; 705/14.53; 705/14.66; 705/14.67

(58) Field of Classification Search
USPC .......... 705/14.23, 14.25, 14.36, 14.38, 14.49, 705/14.51, 14.53, 14.66, 14.67
See application file for complete search history.

(56) References Cited

U.S. PATENT DOCUMENTS

| 3,586,771 | A | 6/1971 | Hamburger ...................... 727/1 |
| 3,961,164 | A | 6/1976 | Reed | |
| 4,650,977 | A | 3/1987 | Couch ........................... 235/379 |
| 4,706,121 | A | 11/1987 | Young | |
| 4,723,212 | A | 2/1988 | Mindrum | |
| 4,910,672 | A | 3/1990 | Off | |
| 5,064,999 | A | 11/1991 | Okamoto et al. ............. 235/379 |

(Continued)

FOREIGN PATENT DOCUMENTS

| EP | 1107100 A1 | 6/2001 |
| WO | WO-01/75678 | 10/2001 |

OTHER PUBLICATIONS

Gilbert, Pat R. Just Push Button for Bus, Park-Ride Ticket. Apr. 15, 1999. The Record. pp. 1-2.*

(Continued)

*Primary Examiner* — Raquel Alvarez
(74) *Attorney, Agent, or Firm* — Blakely, Sokoloff, Taylor & Zafman

(57) ABSTRACT

A method for providing recommendations to a user based on user activity. A plurality of activity data tracking a plurality of activities of a user is obtained. The activity data may be obtained over a wide area network such as the internet or downloaded from a data card which stores activity data whenever the user participates in an activity. The activity data is either stored on the data card or transmitted over the network whenever the user uses a card when participating in any activity such as when making a purchase of goods, paying for services, watching television, etc. The activity data is processed to identify a plurality of user patterns. The user patterns are used to form a user profile and may include user habit data. Recommendations specific to the user based on the user patterns are then created for and provided to the user. The recommendations are provided to a user when the user logs onto a computer network such as the internet. The recommendations may also be provided by electronic mail, electronic pager or other methods. The recommendations are provided by various data analysis techniques including rule based inference engines and other forms of artificial intelligence.

48 Claims, 12 Drawing Sheets

U.S. PATENT DOCUMENTS

| | | | |
|---|---|---|---|
| 5,119,188 A | 6/1992 | McCalley et al. | |
| 5,173,851 A | 12/1992 | Off | |
| 5,410,326 A | 4/1995 | Goldstein | |
| 5,479,268 A | 12/1995 | Young et al. | |
| 5,553,242 A | 9/1996 | Russell et al. | 395/200.12 |
| 5,559,548 A | 9/1996 | Davis et al. | |
| 5,612,868 A | 3/1997 | Off | |
| 5,617,570 A | 4/1997 | Russell et al. | 709/304 |
| 5,625,781 A | 4/1997 | Cline et al. | |
| 5,640,193 A | 6/1997 | Wellner | |
| 5,710,887 A | 1/1998 | Chelliah et al. | |
| 5,727,129 A | 3/1998 | Barrett et al. | |
| 5,734,719 A | 3/1998 | Tsevdos et al. | |
| 5,758,126 A | 5/1998 | Daniels et al. | |
| 5,796,252 A | 8/1998 | Kleinberg et al. | |
| 5,801,702 A | 9/1998 | Dolan et al. | |
| 5,809,204 A | 9/1998 | Young et al. | |
| 5,822,014 A | 10/1998 | Steyer et al. | |
| 5,828,839 A | 10/1998 | Moncreiff | |
| 5,832,457 A | 11/1998 | O'Brien | |
| 5,848,396 A | 12/1998 | Gerace | |
| 5,851,149 A | 12/1998 | Xidos et al. | |
| 5,874,906 A | 2/1999 | Willner et al. | |
| 5,878,222 A | 3/1999 | Harrison | |
| 5,892,827 A | 4/1999 | Beach | |
| 5,896,133 A | 4/1999 | Lynch et al. | |
| 5,900,905 A | 5/1999 | Shoff et al. | |
| 5,902,353 A | 5/1999 | Reber et al. | |
| 5,903,729 A | 5/1999 | Reber et al. | |
| 5,911,145 A | 6/1999 | Arora et al. | |
| 5,915,007 A | 6/1999 | Klapka | |
| 5,918,014 A | 6/1999 | Robinson | |
| 5,925,103 A | 7/1999 | Magallenes et al. | |
| 5,926,795 A | 7/1999 | Williams | |
| 5,933,829 A | 8/1999 | Durst | |
| 5,935,002 A | 8/1999 | Falciglia | |
| 5,956,681 A | 9/1999 | Yamakita | |
| 5,956,693 A | 9/1999 | Geerlings | |
| 5,956,694 A | 9/1999 | Powell | |
| 5,958,012 A | 9/1999 | Battat et al. | |
| 5,960,411 A | 9/1999 | Hartman et al. | |
| 5,974,399 A | 10/1999 | Giuliani | |
| 5,978,381 A | 11/1999 | Perlman et al. | |
| 5,978,773 A | 11/1999 | Hudetz | |
| 5,990,927 A | 11/1999 | Hendricks et al. | |
| 6,002,853 A | 12/1999 | de Hond | |
| 6,003,024 A | 12/1999 | Bair et al. | |
| 6,005,562 A | 12/1999 | Shiga et al. | |
| 6,005,631 A | 12/1999 | Anderson et al. | |
| 6,009,320 A | 12/1999 | Dudley | |
| 6,012,049 A | 1/2000 | Kawan | |
| 6,025,837 A | 2/2000 | Matthews, III et al. | |
| 6,026,370 A | 2/2000 | Jermyn | |
| 6,028,600 A | 2/2000 | Rosin et al. | |
| 6,031,537 A | 2/2000 | Hugh | |
| 6,041,312 A | 3/2000 | Bickerton et al. | 705/30 |
| 6,054,989 A | 4/2000 | Robertson et al. | |
| 6,067,524 A | 5/2000 | Byerly | |
| 6,072,483 A | 6/2000 | Rosin et al. | |
| 6,072,492 A | 6/2000 | Schagen et al. | |
| 6,075,575 A | 6/2000 | Schein et al. | |
| 6,078,866 A | 6/2000 | Buck et al. | |
| 6,091,417 A | 7/2000 | Lefkowitz | |
| 6,094,156 A | 7/2000 | Henty | |
| 6,101,473 A | 8/2000 | Scott et al. | |
| 6,108,656 A | 8/2000 | Durst | |
| 6,112,186 A | 8/2000 | Bergh et al. | |
| 6,129,274 A | 10/2000 | Suzuki | |
| 6,134,548 A | 10/2000 | Gottsman | |
| 6,138,107 A | 10/2000 | Elgamal | |
| 6,142,371 A | 11/2000 | Oneda | |
| 6,148,212 A | 11/2000 | Park | |
| 6,151,050 A | 11/2000 | Hosono et al. | |
| 6,151,059 A | 11/2000 | Schein et al. | |
| 6,151,630 A | 11/2000 | Williams | |
| 6,154,205 A | 11/2000 | Carroll et al. | |
| 6,160,552 A | 12/2000 | Wilsher et al. | |
| 6,172,677 B1 | 1/2001 | Stautner et al. | |
| 6,177,936 B1 | 1/2001 | Cragun | |
| 6,193,152 B1 | 2/2001 | Fernando et al. | |
| 6,198,481 B1 | 3/2001 | Urano et al. | |
| 6,199,048 B1 | 3/2001 | Hudetz | |
| 6,199,098 B1 | 3/2001 | Jones et al. | |
| 6,223,215 B1 | 4/2001 | Hunt et al. | |
| 6,226,623 B1 | 5/2001 | Schein et al. | |
| 6,226,642 B1 | 5/2001 | Beranek et al. | |
| 6,229,540 B1 | 5/2001 | Tonelli et al. | |
| 6,237,030 B1 | 5/2001 | Adams et al. | |
| 6,240,394 B1 | 5/2001 | Uecker | |
| 6,260,192 B1 | 7/2001 | Rosin et al. | |
| 6,266,060 B1 | 7/2001 | Roth | |
| 6,269,343 B1 | 7/2001 | Pallakoff | |
| 6,269,361 B1 | 7/2001 | Davis et al. | |
| 6,269,403 B1 | 7/2001 | Anders | |
| 6,271,832 B1 | 8/2001 | Kamaeguchi et al. | |
| 6,278,979 B1 | 8/2001 | Williams | |
| 6,282,516 B1 | 8/2001 | Giuliani | |
| 6,285,987 B1 | 9/2001 | Roth et al. | |
| 6,286,043 B1 | 9/2001 | Cuomo et al. | |
| 6,288,716 B1 | 9/2001 | Humpleman et al. | |
| 6,292,782 B1 | 9/2001 | Weideman | |
| 6,292,786 B1 | 9/2001 | Deaton et al. | |
| 6,295,057 B1 | 9/2001 | Rosin et al. | |
| 6,298,330 B1 | 10/2001 | Gardenswartz et al. | |
| 6,304,849 B1 | 10/2001 | Uecker | |
| 6,307,958 B1 | 10/2001 | Deaton | |
| 6,312,336 B1 | 11/2001 | Handelman et al. | |
| 6,314,406 B1 | 11/2001 | O'Hagan et al. | |
| 6,321,210 B1 | 11/2001 | O'Brien | |
| 6,330,005 B1 | 12/2001 | Tonelli et al. | |
| 6,330,543 B1 | 12/2001 | Kepecs | |
| 6,333,753 B1 | 12/2001 | Hincley | |
| 6,334,108 B1 | 12/2001 | Deaton et al. | |
| 6,334,145 B1 | 12/2001 | Adams et al. | |
| 6,336,131 B1 | 1/2002 | Wolfe | |
| 6,337,715 B1 | 1/2002 | Inagaki et al. | |
| 6,345,279 B1 | 2/2002 | Li et al. | |
| 6,351,735 B1 | 2/2002 | Deaton | |
| 6,377,935 B1 | 4/2002 | Deaton | |
| 6,388,714 B1 | 5/2002 | Schein et al. | |
| 6,397,387 B1 | 5/2002 | Rosin et al. | |
| 6,401,132 B1 | 6/2002 | Bellwood et al. | |
| 6,411,307 B1 | 6/2002 | Rosin et al. | |
| 6,411,337 B2 | 6/2002 | Cove et al. | |
| 6,417,873 B1 | 7/2002 | Fletcher et al. | |
| 6,418,411 B1 | 7/2002 | Gong | |
| 6,421,066 B1 | 7/2002 | Sivan | |
| 6,421,724 B1 | 7/2002 | Nickerson et al. | |
| 6,430,554 B1 | 8/2002 | Rothschild | |
| 6,434,561 B1 | 8/2002 | Durst, Jr. | |
| 6,438,540 B2 | 8/2002 | Nasr et al. | |
| 6,445,398 B1 | 9/2002 | Gerba et al. | |
| 6,466,918 B1 | 10/2002 | Spiegel | |
| 6,477,575 B1 | 11/2002 | Koeppel et al. | |
| 6,484,146 B2 | 11/2002 | Day | |
| 6,513,015 B2 * | 1/2003 | Ogasawara | 705/26 |
| 6,522,342 B1 | 2/2003 | Gagnon et al. | |
| 6,530,083 B1 * | 3/2003 | Liebenow | 725/46 |
| 6,535,888 B1 | 3/2003 | Vijayan et al. | |
| 6,542,933 B1 | 4/2003 | Durst, Jr. | |
| 6,584,448 B1 | 6/2003 | Laor | |
| 6,587,835 B1 * | 7/2003 | Treyz et al. | 705/14.64 |
| 6,615,248 B1 | 9/2003 | Smith | |
| 6,618,039 B1 | 9/2003 | Grant et al. | |
| 6,631,523 B1 | 10/2003 | Matthews, III et al. | |
| 6,651,053 B1 | 11/2003 | Rothschild | |
| 6,675,165 B1 | 1/2004 | Rothschild | |
| 6,684,062 B1 | 1/2004 | Gosior et al. | |
| 6,684,195 B1 | 1/2004 | Deaton | |
| 6,691,919 B1 | 2/2004 | Katz | |
| 6,692,358 B2 | 2/2004 | Stevens et al. | |
| 6,766,363 B1 | 7/2004 | Rothschild | |
| 6,795,809 B2 | 9/2004 | O'Brien | |
| 6,826,572 B2 | 11/2004 | Colace et al. | |
| 6,829,646 B1 | 12/2004 | Philyaw et al. | |
| 6,965,868 B1 * | 11/2005 | Bednarek | 705/9 |
| 7,058,591 B2 | 6/2006 | Giuliani | |

| | | |
|---|---|---|
| 7,080,070 B1 | 7/2006 | Gavarini |
| 7,228,285 B2 | 6/2007 | Hull |
| 2001/0051903 A1 | 12/2001 | Hansmann et al. |
| 2002/0007309 A1 | 1/2002 | Reynar |
| 2002/0016750 A1 | 2/2002 | Attia |
| 2002/0029339 A1 | 3/2002 | Rowe |
| 2002/0038256 A1 | 3/2002 | Nguyen |
| 2002/0049631 A1 | 4/2002 | Williams |
| 2002/0067376 A1 | 6/2002 | Martin et al. |
| 2002/0078453 A1 | 6/2002 | Kuo |
| 2002/0098834 A1 | 7/2002 | Yuen |
| 2002/0116292 A1 | 8/2002 | Palatin |
| 2003/0046182 A1 | 3/2003 | Hartman |
| 2004/0260689 A1 | 12/2004 | Colace et al. |

OTHER PUBLICATIONS

Winegar, Garvey. Toll-Free Telephone Hotline in Oregon Allows Anglers to Reach Out and Hook Something. Aug. 26, 1993. Richmond Times. pp. 1-3.*

Delta Dental Plan of California Helps Member Dentists Reduce Billing and Insurance Costs With New Technology. Jul. 22, 1998. pp. 1-3.*

Rosenberg, Joyce M. Chasing rates Web sites allow comparison shopping. Mar. 4, 2000. Advocate. p. 1.C.*

Fuhrmans, Vanessa. Insurance: Shopping for Insurance Online Yields Bargains. Aug. 6, 1999. Wall Street Journal Europe. p. 12.*

Susan Decker, "Google Seeks to Invalidate Rival Overture's Web Search Patent," www.Detnews.com, Jun. 20, 2002.

Stephanie Olsen et al. "Overture Sues Google over Search Patent," www.news.com, Apr. 5, 2002.

Danny Sullivan, "Overture Files Patent Lawsuit Against Google," www.searchenginewatch.com, May 6, 2002.

Anon, "Videotron LTEE: Videoway Launches Two New Services: Parental Control and Instant Program Listings," Dec. 13, 1994.

Chieko Asakawa, "User Interface of a Home Page Reader," Apr. 15, 1998, 8 pages, ASSETS '98, Marina del Rey, California.

Charles Heinemann, "Going from HTML to XML," Microsoft Corporation, Nov. 5, 1998.

"How to Know When Your Buddies are Online," AOL, 1997.

Written Opinion dated Jun. 6, 2002, issued in PCT/US00/30248.

Network Working Group; Request for Comments: 1738; T. Berners-Lee; Dec. 1994; 24 pages.

Network Working Group; Request for Comments: 2396; T. Berners-Lee; Aug. 1998; 1 page.

PCT Written Opinion; Int'l filing date—Oct. 31, 2000; Int'l application No. PCT/US00/30248; 12 pages.

* cited by examiner

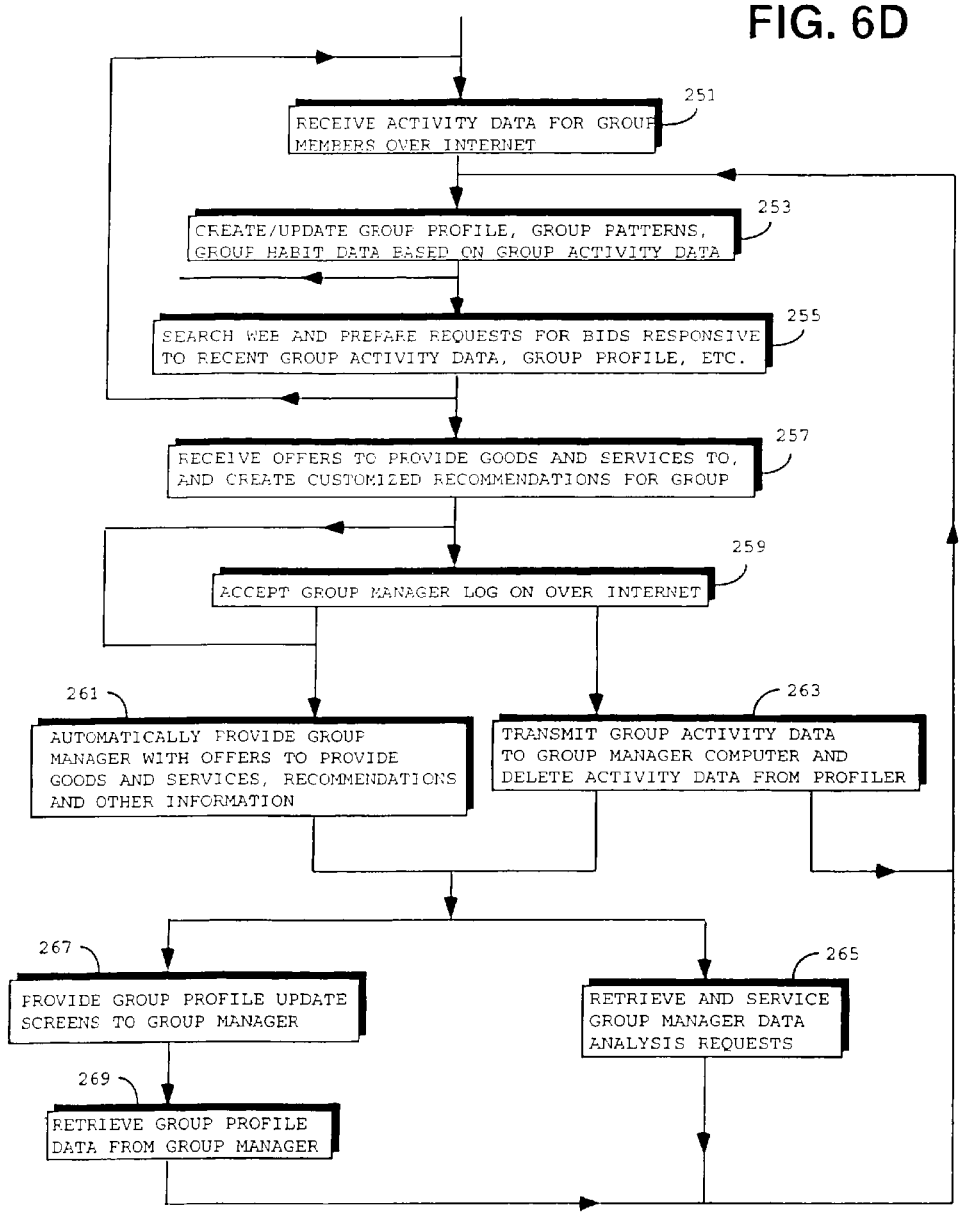

METHOD FOR PROVIDING INFORMATION AND RECOMMENDATIONS BASED ON USER ACTIVITY

This is a divisional of patent application Ser. No. 09/525,235, filed on Mar. 15, 2000 now U.S. Pat. No. 6,611,881, entitled A METHOD FOR PROVIDING INFORMATION AND RECOMMENDATIONS BASED ON USER ACTIVITY.

BACKGROUND

1. Field of the Invention

The invention relates to a method for customizing searches of the internet. More specifically, the invention relates to a method for searching the internet and providing customized recommendations responsive to a user's real world activities.

2. Background

The internet is ubiquitous in popular culture. As more and more people go on-line and begin experiencing what the internet has to offer, more and more people are becoming frustrated with the huge amount of data available for consumption via the enormous number of web sites existing in cyberspace. This includes users at home or at work using the internet to pursue hobbies, do homework, do research for school or work projects, etc.

After a user establishes a connection with the internet, the user typically wants to find information of some sort. A common method of finding information on the internet is by using one of the plethora of internet web search engines, e.g., ALTAVISTA.COM, GO.COM, and GOTO.COM. After entering key words describing a concept, thing or event, a multitude of web sites are provided to the user. However, because of the enormous number of web sites that exist in cyberspace, all but the most specialized requests return at least hundreds, typically thousands, and often tens of thousands of web sites. The order in which the web sites are presented is determined by rules at the search engine or randomly. One such rule is based on fees paid by web sites to be listed with the search engine such that the entities paying the larger sums have their web sites displayed on the top of the list provided to the user, e.g., GOTO.COM.

To assist users in beginning to manage the enormous amount of data available on the internet, many web sites provide a rudimentary customization of information for the user. These rudimentary customizations are, however, limited to selection and organization of the information available on the particular web sites and not over the entire internet. For example, shopping web sites allow users to select favorite product areas, choose favorite designers and manufacturers, specify user information such as sizes and colors, etc. (e.g., BLUEFLY.COM). Other examples include news sites which display categories of news based on user specified interest areas and user information such as geographical location. (e.g., MYPAGE.GO.COM).

Internet activity of users is monitored by various companies that track usage patterns of internet web surfers. Web site operators use this information to direct adds to users based on typical web surfing patterns. These advertisements are, thus, responsive to users' interests as reflected in web site visitations. However, consumers and businesses do not have access to this information.

In the real world, the activities of persons and businesses are also tracked to a limited extent. For example, when a consumer makes purchases at a grocery or drug store, consumers often swipe a personal identification card to obtain discounted prices. Similarly, when purchases are made by consumers and businesses at membership only stores, a membership identification card is presented. In this way, retailers track information about and monitor the buying habits of their customers. However, consumers and businesses do not have access to this information.

The real world of bricks and mortar stores and cyberspace are beginning to overlap. Companies are now producing internet connected cash registers which have instant access to inventory and the company's web site, including web placed orders. To authorize a credit card transaction, cash register computers connected to the internet obtain automatic authorization of credit card purchases via the internet. In addition, to give users confidence in the security of transactions over the internet and to ease making purchases on the internet, credit card companies have developed credit cards which can be inserted into card readers attached to user's personal computers which authorize and ease on-line purchases.

Although the internet promises to be pervasive in our society, credit cards already are. Consumers routinely use credit cards to pay for any kind of transaction imaginable, from purchasing groceries, to paying for a dental exam, to buying movie tickets. Businesses also use credit cards for purchasing employee travel, office supplies, office equipment, etc. When credit card transactions are transmitted to the credit card issuer, limited information such as the total amount of the transaction and the name of the entity to be credited are maintained. In this way, general buying habits are monitored and maintained by credit card companies and are offered for sale. However, consumers and businesses do not have access to this information.

Consumers and groups of consumers have not benefited from and do not have access to the plethora of information maintained about them by retailers, credit card companies, internet tracking companies, and others. Similarly, businesses have not benefited from and do not have access to the plethora of information maintained about them and their employees by retailers, credit card companies, internet tracking companies, and others.

BRIEF SUMMARY OF THE INVENTION

A method for providing recommendations to a user based on user activity. A plurality of activity data tracking a plurality of activities of a user is obtained. The activity data may be obtained over a wide area network such as the internet or downloaded from a data card which stores activity data whenever the user participates in an activity. The activity data is either stored on the data card or transmitted over the network whenever the user uses a card when participating in any activity such as when making a purchase of goods, paying for services, watching television, etc. The activity data is processed to identify a plurality of user patterns. The user patterns are used to form a user profile and may include user habit data. Recommendations specific to the user based on the user patterns are then created for and provided to the user. The recommendations are provided to a user when the user logs onto a computer network such as the internet. The recommendations may also be provided by electronic mail, electronic pager or other methods. The recommendations are provided by various data analysis techniques including rule based inference engines and other forms of artificial intelligence.

BRIEF DESCRIPTION OF THE DRAWINGS

FIG. 6D illustrates the activities of a profiler system profiler server when used by a group and a group manager.

DETAILED DESCRIPTION

As credit card use is pervasive and as the internet is becoming more and more popular, various embodiments of this invention combine certain elements of both to increase the user's enjoyment of the internet by making the internet more useful. To achieve this, the user of the internet is provided a data card. The data card is a transportable recordable medium (TRM) known to those skilled in the art. In one embodiment, the TRM may include a magnetic strip containing data and a writeable memory device. In another embodiment, the TRM may be comprised of a writeable memory device. In either of these embodiments, the TRM may also include transmitting and receiving means for sending and receiving the data stored on the memory device portion of the TRM. Generally, whenever the user participates in any activity, the user presents the data card, and information about the activity is either stored on the card or transferred over the internet to a profiler server. The profiler system then provides customized data and web site references to the user. The profiler may also be used to assist groups such as groups of neighbors or relatives, or a business. In such embodiments, the profiler can search and locate bulk discounts and automatically request bids for goods and services regularly purchased based on group members' real world activities.

Figure 1A:
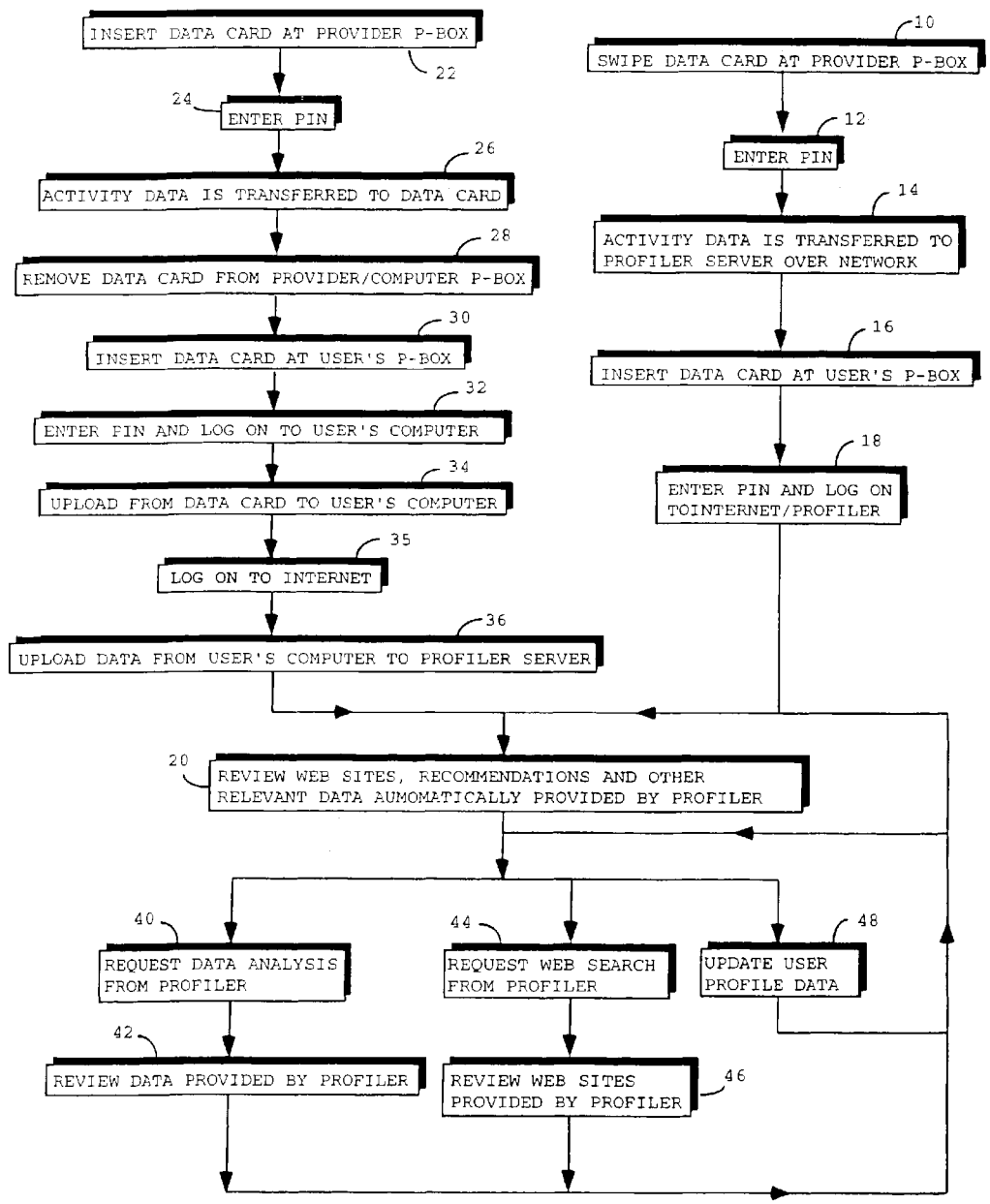
FIG. 1A illustrates the activities performed by a profiler system user.

A. Using a Profiler System to Retain Activity Data and Provide Customized Recommendations FIG. 1 illustrates the activities performed by a profiler system user. In one embodiment, every provider of any and all goods, services, entertainment, etc. maintains a cash register or computer coupled with or including a device to read, and in some embodiments, write, to the data card. Devices for reading from and writing to the data card are denoted p-boxes, short for profiler boxes. The p-boxes allow for reading from and/or writing to, and in some embodiments transmitting data to and receiving data from, the data card. In one embodiment, whenever a user makes a purchase at a retail establishment, pays for services rendered, etc., the user presents the data card, swipes the card at a p-box, that is, slides it through a data card reader, as shown in block 10. After swiping the card, the user then authorizes access to the data card and its features. In one embodiment, this is achieved by the user entering a personal identification number (PIN), such as by typing onto a key pad, as shown in block 12. The PIN is then compared to an encoded, previously stored PIN on the data card or stored on the profiler server. In another embodiment, a finger print of the user is scanned and compared with data stored either on the data card or on the profiler server to authenticate use of the data card. In addition, in other embodiments, authorization may be achieved by any method known to those skilled in the art, including but not limited to retinal scan and voice print recognition.

In one embodiment, the data card is swiped in addition to making payment by any traditional method. That is, the data card is swiped in addition to swiping a credit card or debit card or paying with cash or bank check. In such an embodiment, activity data reflecting the activity is transferred to a profiler server via a wide are network (WAN) such as the internet, as shown in block 14. In one embodiment, this transfer of activity data is transparent to the user. In various embodiments, transmission of activity data over the internet may be done securely by any encryption method known to those skilled in the art. In this way, the user's activity data remains private.

Activity data provides details about the activity entered into by the user. In one embodiment, activity data may include retail transaction data such as what items were purchased in what quantity and at what price. For example, when grocery shopping, each item purchased, the quantity of the items, and the price for the items is included as activity data. Another example of activity data is service provider data such as what service was provided and at what price. Examples of services are numerous and include car wash, hair cut, gardening, maid service, plumbing repair, roof repair, and so on. If when making a purchase the user wants to keep the activity private or hidden from the profiler system, all the user need do is not swipe the data card.

After participating in some activities, the user then goes home and, in one embodiment, inserts the data card at a p-box attached to the user's personal computer, as shown in block 16. The user's computer may be any computing device such as a cellular telephone, portable computer, electronic personal organizer, desktop computer, dedicated internet device, etc. with access to a WAN such as the internet. In addition, the location of the personal computing device is not limited to the home, but may be any location convenient to the user, including, but not limited to home, car, office, shopping mall, park, beach, etc. In this embodiment, to access the activity data transmitted when making payment for a transaction, a user's computer includes a p-box. The p-box may be included in or attached to the user's computing device. The user then authorizes access to the data card and the profiler system. In one embodiment, the user achieves this authorization by entering a PIN and logging on to the profiler server via the internet, as shown in block 18. Immediately upon connecting to the profiler server, the user is automatically provided web sites, recommendations and other relevant information as shown in block 20. The web sites and recommendations provided by the profiler server are customized to the user and are based on user patterns such as buying habits, eating habits, entertainment habits, and others culled from examining and processing the user's activity data.

In another embodiment, the data card is not just read but is written to when the user pays for good or services, or pays for entertainment or participates in any activity. In this embodiment, the p-boxes are data card readers/writers. Whenever a user makes a purchase at a retail establishment, pays for services rendered, etc., the user presents the data card by inserting it into a provider p-box, as shown in block 22. After inserting the data card, the user then authorizes access to the data card and its features. In one embodiment, this is achieved by entering a PIN, as shown in block 24. In this embodiment, the data card is used in addition to making payment by any traditional method. In such an embodiment, activity data reflecting the activity is transferred to the user's data card, as shown in block 26. That is, activity data providing details about the activity is written onto the data card according to any method known to those skilled in the art. In various embodiments, activity data is stored securely on the data card by any encryption method known to those skilled in the art. In this way, the user's activity data is protected from dissemination in the event the card is lost or stolen. As above, if when making a purchase the user wants to keep the activity hidden, all the user need do is not insert the data card.

The data card of the profiler system may also be used when participating in activities for which no payment is made. One example of this involves watching television and using a home television monitor. In one embodiment, when watching television, a data card is placed in the television and activity data is either stored on the card or transmitted to the profiler server. In this embodiment, activity data includes the program watched, the channel watched, the time of day the program aired, and the length of time the television was turned on. In a related embodiment, when using a television connected to a video tape player, video disc player, cable box or satellite dish, the user places the data card in a data card enabled video tape player, video disc player, cable box or satellite box such that activity data regarding the programs watched is recorded onto the data card. In another embodiment, the activity data is transmitted to the profiler server over the internet via any connection to the internet known to those skilled in the art, including, but not limited to a television cable, a satellite connection, a digital subscriber line (DSL), T1 lines, etc.

Another example of activities not involving payment for which the data card is used is using the data card when in a motor vehicle such as a car or truck. In this embodiment, information about the vehicle's systems and use of the vehicle is stored on the data card. In this embodiment, the activity data may include, but is not limited to, at what time of day the vehicle is driven, for what period of time the vehicle is in operation, and for what distance the vehicle is driven. In a related embodiment, the data card is used as an access device such that the car cannot be started unless the data card is inserted into a data card receiver located in the vehicle. In such an embodiment, a PIN or other form of authorization may also be required in conjunction with the data card to allow for starting the motor vehicle.

Yet another example of activities not involving payment for which the data card is used is using the data card when making telephone calls, both with cellular telephones and with traditional telephones connected to fixed lines. In such embodiments, the telephone includes a data card receiver that records activity data about the phone calls made. Such phone activity data may include, but is not limited to, the phone numbers called, the length of the call, and the telephone carrier used. In a related embodiment, the data card is used as an access device such that the telephone cannot be used unless the data card is inserted into a data card receiver located in the phone. In such an embodiment, a PIN or other form of authorization may also be required in conjunction with the data card to allow for using the telephone.

After participating in some activities, the user then goes home and inserts the data card at a p-box attached to the user's personal computer, as shown in block 30. The user then authorizes use of the profiler system by entering a PIN or performing another form of authorization when logging on to the profiler application program on the user's computer, as shown in block 32. In one embodiment, upon connecting to the profiler application program, the activity data is uploaded from the data card to the user's computer, as shown in block 34. In one embodiment, the uploading is automatic and may be hidden from the user. In another embodiment, the profiler application program asks the user if the user would like to transfer activity data from the data card to the user's computer. After logging onto the internet, as shown in block 35, the new activity data is then uploaded from the user's computer to the profiler server, as shown in block 36. In one embodiment, the uploading is automatic and may be hidden from the user. In another embodiment, the profiler application program asks the user if the user would like to transfer activity data from the user's computer to the profiler server.

Upon connecting to the profiler server, and after uploading new activity data, the user is automatically provided web site recommendations and other relevant information tailored to the user, as shown in block 20. The customized web site recommendations and other data are reflective of the user's lifestyle and are based on the user profile which is culled from the activity data, and derived, inferred and extrapolated from user patterns and habits. In one embodiment, user profile data provided by the user may also be used in determining the recommendations and data.

In one embodiment, the web sites are arranged on the user's screen grouped in categories and may be placed in multi-layered folders, or arranged in other ways known to those skilled in the art. In another embodiment, the user may customize how and in what format or organization the recommendations and information are displayed. In one embodiment, the arrangement is based on examination and evaluation of user patterns culled from the activity data. In another embodiment, the arrangement is designated by the user in a user profile and determined by the profiler server in conjunction with the user's interests based on examination and evaluation of user patterns culled from the activity data. The user then proceeds to investigate the various web sites listed and view the recommendations and relevant data, as shown in block 20.

Examples of web site recommendations and relevant data which the user receives are numerous. In one embodiment, text and/or graphical icons are displayed representing categories or groupings of recommendations and data, and the user selects a category or grouping by clicking on the text or icon according to methods known to those skilled in the art. For example, in one embodiment when the user clicks on the entertainment category, the user receives a list of recommended newly released compact discs, upcoming concerts, upcoming television and cable shows of interest, as well as information about favorite entertainers. In one embodiment, this information may be displayed immediately, or in another embodiment, a grouping of icons representing sub-categories may appear from which the user chooses by clicking on to obtain the information listed in the prior sentence. In yet another embodiment, textual information of interest will be displayed adjacent to links to related web sites. The recommendations and information provided are reflective of the user's habits and interests as they are derived from the user's activity data, user patterns, habit data and/or the user profile.

Figure 1B:
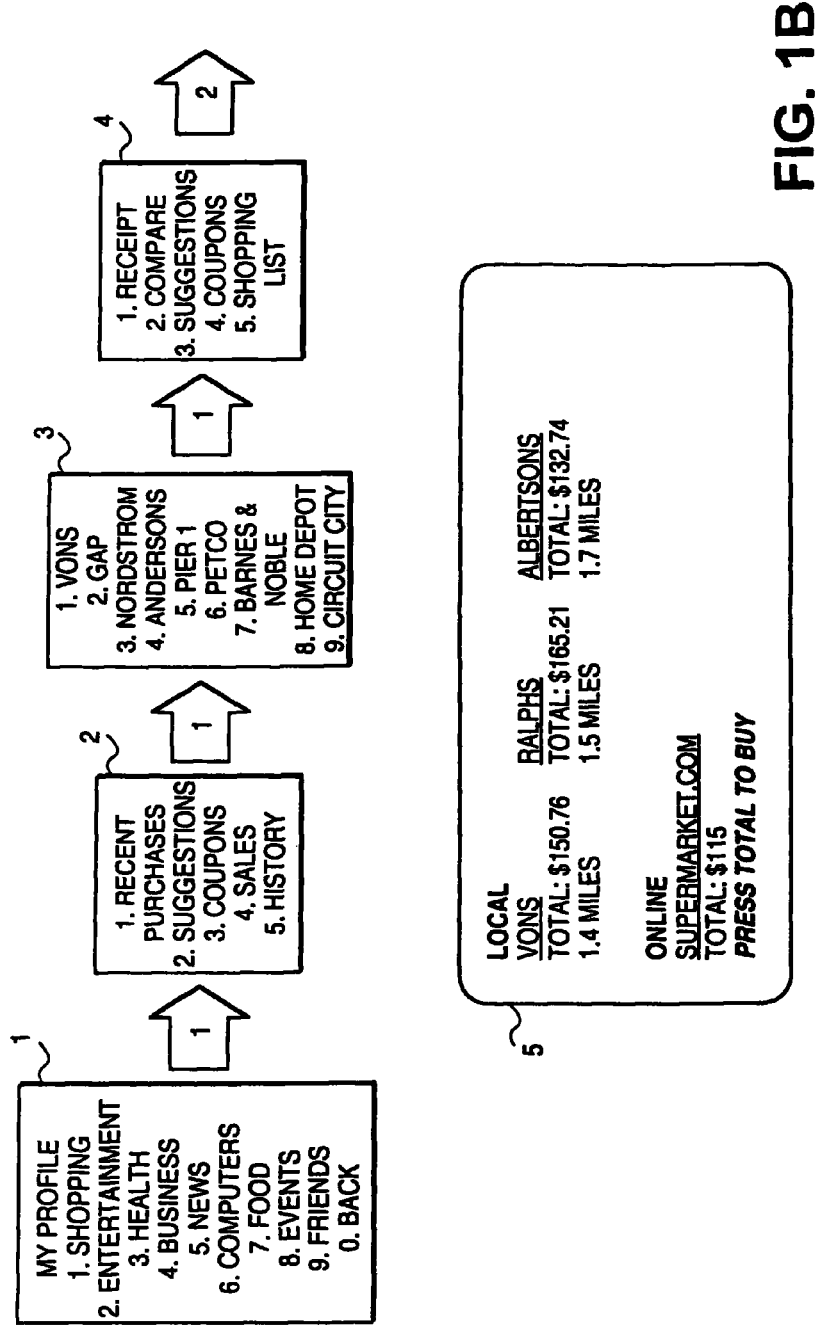
FIG. 1B illustrates an example of the information and recommendations provided to a profiler system user after logging on to the profiler system.

FIG. 1B illustrates an example of the information and recommendations provided to a profiler system user after logging on to the profiler system. In this example, a portion of the user's display contains a list of categories or groupings including, but not limited to, shopping, entertainment, health, business, news, computers, food, events and friends, as shown in block 1. In another embodiment, the list may not be a list, but may be a grouping of icons. After selecting "shopping" by clicking on the text or an icon representation, the user then sees a new list of sub-categories, this one comprising recent purchases, suggestions, coupons, sales, and history, as shown in block 2. If the user selects "recent", a list of stores at which the user recently shopped is displayed, as shown in block 3. If the user clicks on "Vons", a new list of sub-sub-categories is displayed showing receipt, compare, suggestions, coupons, and shopping list, as shown in block 4. If the user selects "compare", in one embodiment, the profiler system takes the most recent Vons purchases, obtains prices for the same items from other local grocery stores, as well as one on-line merchant, and provides the results to the user, as shown in block 5. In this embodiment, the distance from the particular stores is also displayed, and with regard to the on-line store, the user only needs to click on the total (or other associated region of the on-line merchant area of the display) to initiate purchasing the same items that were recently purchased at Vons.

Figure 1C:
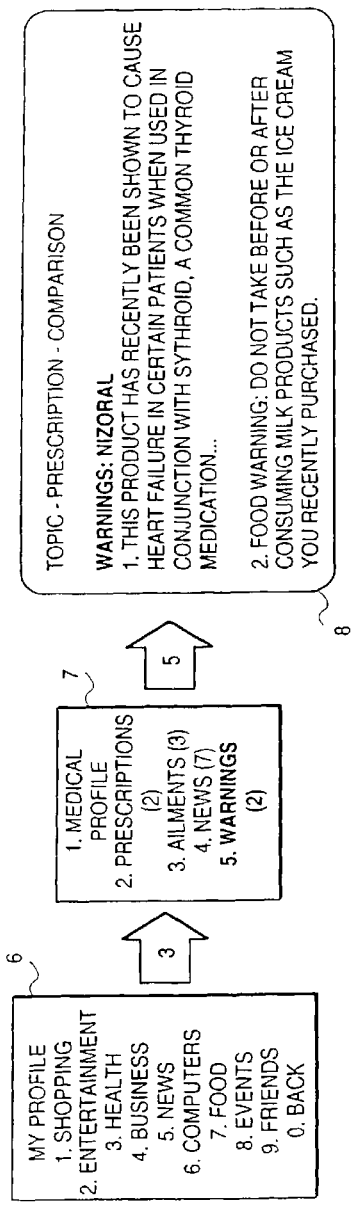
FIG. 1C illustrates another example of the information and recommendations provided to a profiler system user after logging on to the profiler system.

FIG. 1C illustrates another example of the information and recommendations provided to a profiler system user after logging on to the profiler system. In this example, the user selects "health" by clicking on the text or a health icon from a list or grouping of icons representing categories, as shown in block 6. The user is then presented with a list or grouping of sub-categories and selects "WARNINGS", as shown in block 5. The profiler system then provides a window or display area that lists health warnings, as shown in block 8. In this example, the profiler system determined from the activity data that the user was prescribed and/or had purchased the drug Nizrol. The profiler system then processed this information, issued internet queries and/or consulted its own database, and provided a drug warning concerning the side effects of the drug. In addition, the profiler system also cross-referenced certain data it received about the drug with the user's recent activity data, which included an ice cream purchase, and prepared a warning about when the medication should be taken. That is, because retrieved drug data stated that the medication should not be taken with milk products, the profiler system issued a warning to the user not to take the drug when eating recently purchased ice cream.

In another embodiment, upon logging on to the profiler system, the user is also provided email messages providing recommendations and relevant information based on user patterns and habit data derived and extrapolated from the activity data. Such email may be sent to the user at any time, and the user receives such email when checking email by any method known to those skilled in the art, such as for example, via cellular telephone or other portable computing device. In yet another embodiment, the user may receive electronic pages or other transmissions from the profiler system via any method known in the art, including email, that provide pertinent information and recommendations. In either or both of the prior embodiments, the information and recommendations may be, for example, airline flight time data, an alert not to eat certain purchased food based on health data, or product recall notice information regarding recently purchased products. In yet another embodiment, the user's email may be sorted into categories by the profiler system, directed into themed groupings and presented with and under the categories of information and recommendations provided when logging on. In a related embodiment, the user's email may be sorted and stored by the profiler system as themed mail boxes or stored under themed icons in the mailer program.

In addition, when logged on to the internet, in one embodiment, the user can choose from various personal analysis programs to evaluate the user's buying and other habits. In one embodiment, the personal analysis programs are provided as plug-ins to the profiler application program such that additional plug-ins can be either purchased or downloaded by the user. In another embodiment, the personal analysis programs are provided by the profiler server as special purpose mini-application programs, such as JAVA applets, that are downloaded when the user requests a particular personal analysis program. In one embodiment, the personal analysis programs evaluate data stored on the user's personal computer. In another embodiment, the personal analysis programs evaluate data stored on or uploaded to the profiler server.

An example of a personal analysis program is a personal accounting profiler. Upon obtaining and running the personal accounting profiler, in one embodiment, the user invokes the personal accounting profiler from a pull-down menu and/or by clicking on a graphically displayed icon. When the personal accounting profiler opens on the user's screen, the user may request it to perform any one of a number of typical and helpful accounting tasks. In one embodiment, the user requests the personal accounting profiler to examine activity data to determine the amount of money spent in one of a plurality of categories, including, but not limited to, dining out, gasoline, entertainment, video rentals, etc. over a specified period of time, such as the last week, last month, last year, or a defined period with a start and end date. The user interface may be any interface known to those skilled in the art including, but not limited to, pull-down menus, text tags adjacent to buttons, pull-down bars, sliders, etc. In addition, other analysis options may be provided, such as to provide all potential tax deductions as derived from the activity data. In one embodiment, the personal accounting profiler runs while the user is connected to the internet, and the activity data is obtained from a profiler server. In another embodiment, the user need not be connected to the internet when running the personal accounting profiler, and activity data is accessed from the user's personal computer.

Another example of a personal analysis program is a personal shopping profiler. Upon obtaining and running the personal shopping profiler, in one embodiment, the user invokes the personal shopping profiler from a pull-down menu and/or by clicking on a graphically displayed icon. When the personal shopping profiler opens on the user's screen, the user may request it to perform any one of a number of helpful analysis tasks. In one embodiment, the user requests the personal shopping profiler to examine activity data to determine the amount of money spent on one of a plurality of categories or kinds of clothing, including, but not limited to, shirts, blouses, pants, suits, underwear, panties, ties, shoes, dress shoes, athletic wear, athletic shoes, dress shoes, etc. over a specified period of time, such as the last month, last year, or a defined period with a start and end date. The personal shopping profiler may also allow for analysis of brands purchased, or provide a list of all items purchased manufactured by a specified company or from a specified retailer. More detailed analysis may also be provided such as providing a list of all clothing purchased made from cotton, from where it was purchased, and when; or providing a list of what foods containing milk were purchased, from what store, and when. In one embodiment, the personal shopping profiler runs while the user is connected to the internet, and the activity data is obtained from a profiler server. In another embodiment, the user need not be connected to the internet when running the personal shopping profiler, and activity data is accessed from the user's personal computer.

Referring again to FIG. 1A, with regard to any of these embodiments, the user requests analysis from the profiler system, either the profiler server or the profiler application program, as shown in block 40. After providing any additional information required by the personal analysis program, the personal analysis program runs, and the user then reviews the data provided, as shown in block 42.

Further, when the user is logged on to the internet, in one embodiment, the user may request a web search from the profiler server, as shown in block 44. After initiating a web search, the profiler filters and evaluates the multitude of web pages responsive to the search and only provides the most pertinent web sites to the user based on the user patterns culled from the activity data. The user then reviews the web sites provided by the profiler server, as shown in block 46.

Furthermore, in one embodiment, after entering basic user data into a user profile upon initially using the profiler system, or, in another embodiment, after the profiler server has created a user profile for the user, the user has the opportunity to update the user profile data whenever the user chooses, as shown in block 48. A user may choose to update the user profile for any number of reasons, such as to change a work or home address, to change color or brand preferences, to change weight or size information, etc. The user profile is discussed in more detail below with regard to the profiler server.

Figure 2A:
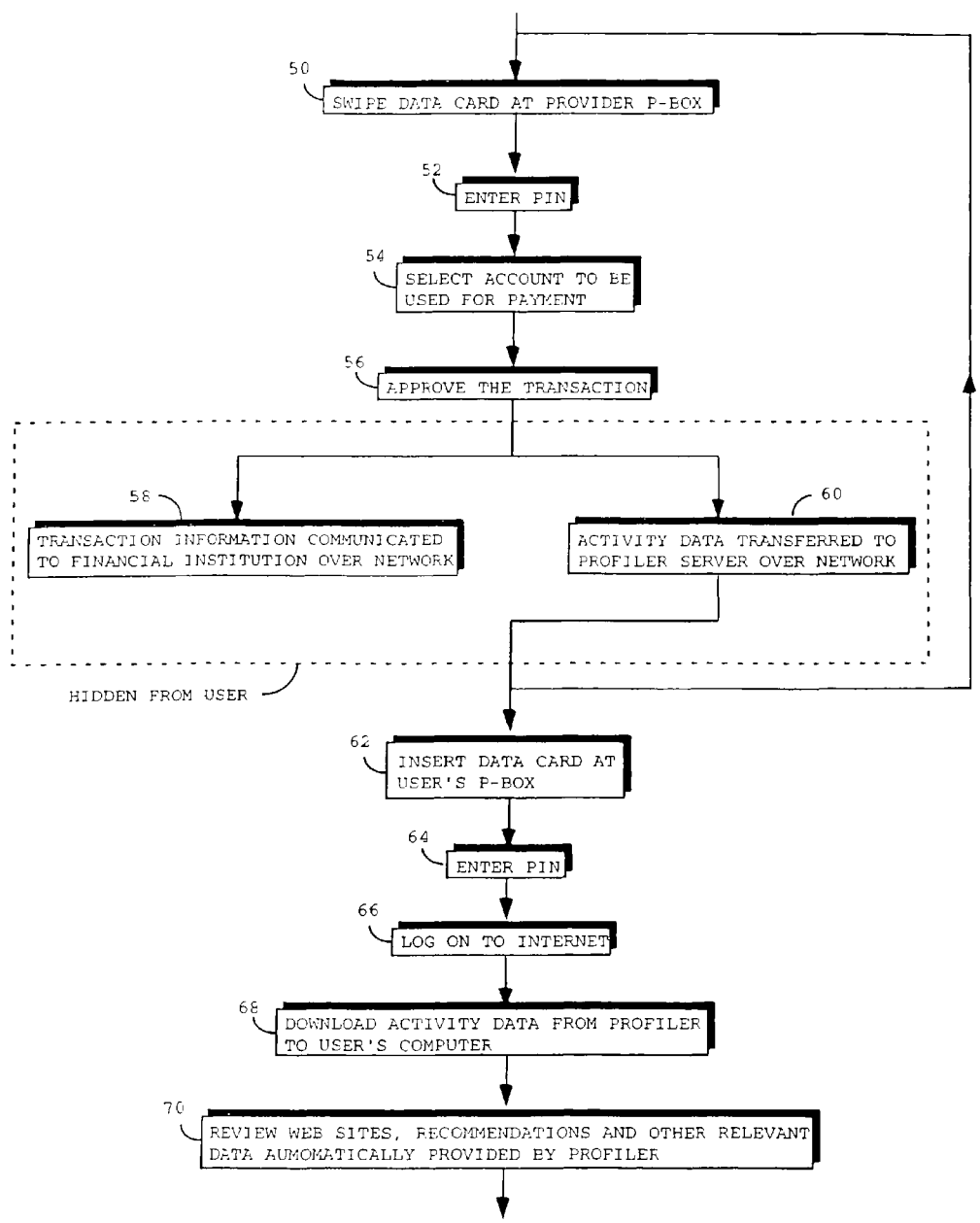
FIG. 2A illustrates the activities performed by a profiler system user in which financial transaction information and activity data are communicated via the internet.

B. Using the Profiler System to Retain Activity Data, Make Payments and Provide Customized Recommendations that May Include Offers from Suppliers of Goods and Services FIG. 2A illustrates the activities performed by a profiler system user in which financial transaction information and activity data are communicated via the internet. In this embodiment, the data card is used to make a payment similar to a traditional transaction involving a credit card or a debit card. In this embodiment, when making any payment, the user presents the data card and swipes the card at a p-box, as shown in block 50. After swiping the card, in one embodiment the user then authorizes access to the data card and its features by entering a PIN or performing another form of authorization, as shown in block 52. The user then is provided with a list of accounts from which to choose. Payment for the transaction will then be taken from or debited to the selected account. The list of accounts, in one embodiment, is obtained from the profiler server over the internet. The accounts are any accounts the user has previously selected to be accessible via the data card when setting up or editing a user profile. The accounts may be credit card accounts, bank checking accounts, bank savings accounts, money market or any other accounts from any number of financial institutions or entities. The user then selects an account to be used for payment of the transaction, as shown in block 54. The user then approves the transaction, as shown in block 56, by, in one embodiment, responding to a question displayed on a screen asking the user to confirm that a specified total amount of the transaction will be drawn from the specified account.

In one embodiment, after the user approves the transaction, information about the financial transaction is transmitted to the financial institution over the internet, as shown in block 58. In addition, activity data is transferred to a profiler server via the internet, as shown in block 60. The transmission to the financial institution and the profiler server may both be hidden from the user.

After participating in some activities, the user then goes home and inserts the data card at a p-box attached to the user's personal computer, as shown in block 62. The user then authorizes access to the profiler system by entering a PIN or performing another form of authorization when logging on to the profiler server via the internet, as shown in blocks 64 and 66. In one embodiment, upon connecting to the profiler server, activity data that has been collected by the profiler server when the user was participating in activities is automatically downloaded to the user's computer, as shown in block 68. In this embodiment, activity data is only temporarily stored on the profiler server so that only the user maintains a full set of activity data such that only the user has access to and control of the personal activity data. In such an embodiment, the profiler server maintains only user habit data, user patterns, and/or the user profile. This provides added privacy to the system so that a user does not worry about what continued use the profiler server is making of the activity data. In addition, in another embodiment, the user may select and delete activity data items on the user's personal computer. In this way sensitive, personal activity data of any kind can be removed so that no one has access to it. Upon logging on to the profiler system, the user is then automatically provided web sites, recommendations and other information tailored to the user, as shown in block 70.

To address privacy and security concerns of profiler system users, in other embodiments, the user may choose what kind of access should be allowed to the data card during the current transaction or activity. In one embodiment, for example, the user may want to opt out of the payment function of the data card. In such an embodiment, before account information is displayed, the user chooses whether payment will be made via the data card or will be made external to the data card, that is by a traditional method such as credit card, debit card, cash or bank check. In another related embodiment, the password entered by the user automatically designates the level of use of the data card. In such an embodiment, when initializing the card, the user may set passwords which, when entered, automatically block access to financial accounts while allowing access to basic personal information and causing activity data to be stored on the data card and/or transferred. In other embodiments, there may be multiple levels of access to the card based on a plurality of passwords. For example, one password may allow access to health and medical information stored on the data card; another may allow access to health and medical information as well as financial data; yet another may only allow for activity data to be transferred over the internet to the user's account on a profiler server or onto the data card; and yet another may allow for financial data to be accessed and for activity data to be transferred.

Figure 2B:
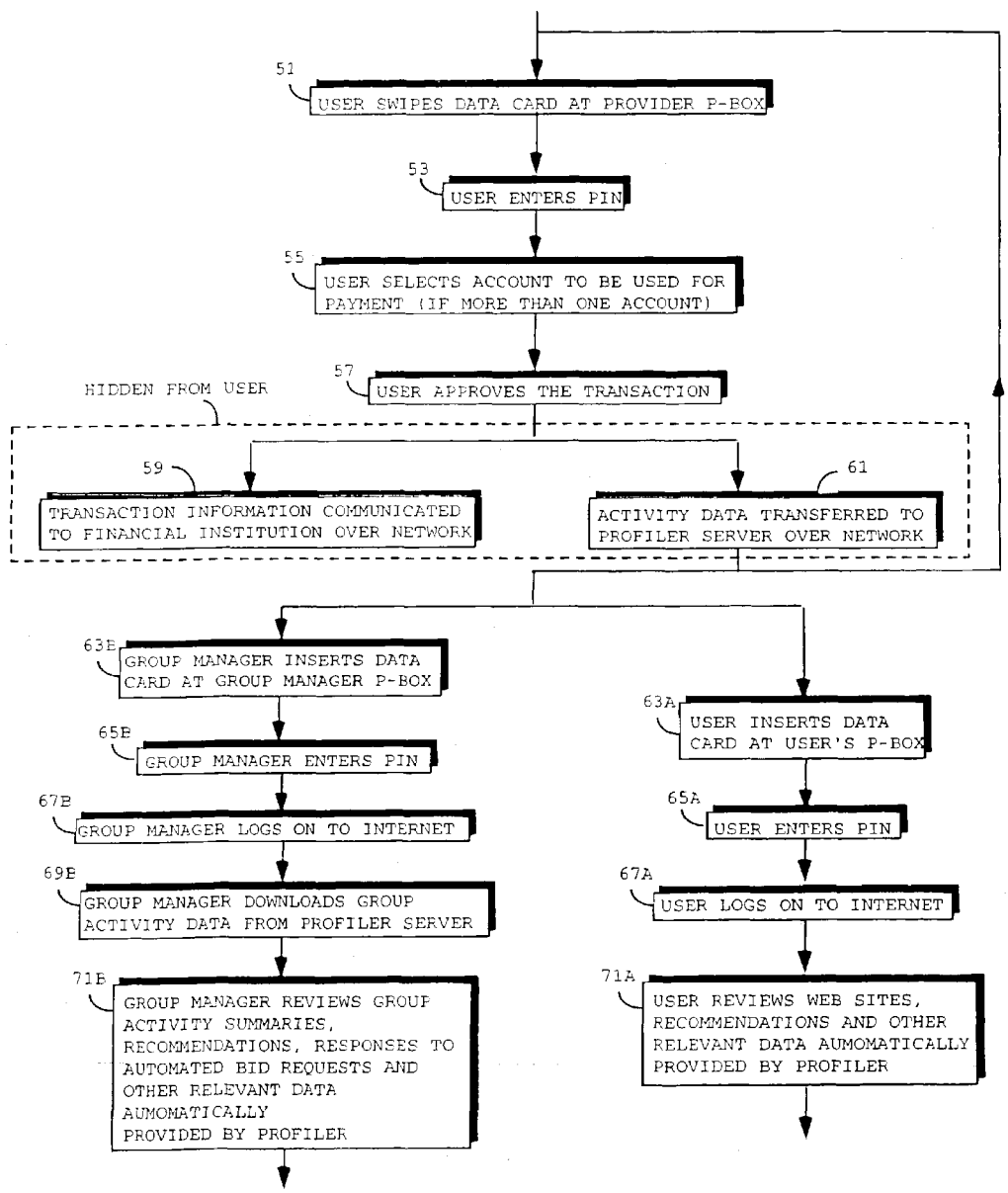
FIG. 2B illustrates the activities performed by a profiler system user and group manager in which financial transaction information and activity data are communicated via the internet.

FIG. 2B illustrates the activities performed by a profiler system user and group manager in which financial transaction information and activity data are communicated via the internet. In this embodiment, the profiler system user is a member of a group. In one embodiment, a group may be a business entity such that the group members are employees and staff. In another embodiment, a group may be a collection of neighbors from a neighborhood. In yet another embodiment, the group may be a collection of relatives. In still another embodiment, the group may be a collection of businesses such that there are sub-groups of businesses. In any of these embodiments, a data card is used to make a payment similar to a traditional transaction involving a credit card or a debit card. In this embodiment, when making any payment, the user presents the data card and swipes the card at a p-box, as shown in block 51. After swiping the card, in one embodiment the user then authorizes access to the data card and its features by entering a PIN or performing another form of authorization, as shown in block 53. The user then is provided with a list of accounts from which to choose. Payment for the transaction will then be taken from or debited to the selected account. The list of accounts, in one embodiment, is obtained from the profiler server over the internet. The accounts are any accounts the user has previously selected to be accessible via the data card when setting up or editing a user profile. The accounts may be credit card accounts, bank checking accounts, or any other accounts from any number of financial institutions or entities. In one embodiment, the user is only provided the accounts to which the user has been granted access. In another embodiment, if there is only one account, this step may be skipped. In addition, in the neighborhood group and relative group embodiments, only the particular user's accounts may be provided to the particular user such that privacy is maintained by the group members. In the business group context, the particular user is only provided a list of accounts to which the particular user has been given access. In other embodiments, both business and personal accounts may be listed.

The user then selects an account to be used for payment of the transaction, as shown in block 55. The user then approves the transaction, as shown in block 57, by, in one embodiment, responding to a question displayed on a screen asking the user to confirm that a specified total amount of the transaction will be drawn from the specified account.

In one embodiment, after the user approves the transaction, information about the financial transaction is transmitted to the financial institution over the internet, as shown in block 59. In addition, activity data is transferred to a profiler server via the internet, as shown in block 61. The transmission to the financial institution and the profiler server may both be hidden from the user.

After participating in some activities, the user then goes home or to work (or any other location) and inserts the data card at a p-box attached to the user's computer, as shown in block 63A. The user then authorizes access to the profiler system by entering a PIN or performing another form of authorization when logging on to the profiler server via the internet, as shown in blocks 65A and 67A. Upon logging on to the profiler system, the user is then automatically provided web sites, recommendations and other information tailored to the user, as shown in block 71A.

To address privacy and security concerns of profiler system users, particularly in the neighborhood group and relative group embodiments, and in other embodiments, the user may choose what kind of access should be allowed to the data card and activity data during the current transaction or activity. In one embodiment, the password entered by the user automatically designates the level of use of the data card. In such an embodiment, when initializing the card, the user may set passwords which, when entered, automatically block access to financial accounts while allowing access to basic personal information and causing activity data to be stored on the data card and/or transferred. In other embodiments, there may be multiple levels of access to the card based on a plurality of passwords. For example, one password may allow access to health and medical information stored on the data card; another may allow access to health and medical information as well as financial data; yet another may only allow for activity data to be transferred over the internet to the user's account on a profiler server or onto the data card; and yet another may allow for financial data to be accessed and for activity data to be transferred. Moreover, in yet other embodiments, other passwords will automatically block transfer of activity data from the group account on the profiler system but allow transfer of the activity data to the user's personal account on the profiler system.

When a group such as a business or non-business group is established on the profiler system, in one embodiment, a group manager or multiple group managers are designated. In such an embodiment, the group manager is given access to the group activity data and recommendations and other information provided by the profiler system. Just as with regular profiler system users, the group manager accesses the profiler system when at home or at work (or any other location) by first inserting the data card at a p-box attached to the group manager's computer, as shown in block 63B. The group manager then authorizes access to the profiler system by entering a PIN or performing another form of authorization when logging on to the profiler server via the internet, as shown in blocks 65B and 67B. In one embodiment, upon connecting to the profiler server, group's activity data that has been collected by the profiler server when the group members were participating in activities is automatically downloaded to the group manager's computer, as shown in block 69B. In this embodiment, group activity data is only temporarily stored on the profiler server so that only the group manager maintains a full set of activity data such that only the group manager has access to and control of the group activity data. In such an embodiment, the profiler server maintains only group habit data, group patterns, and/or the group profile. This provides added privacy to the system so that a group manager does not worry about what continued use the profiler server is making of the group activity data. In addition, in another embodiment, the group manager may select and delete activity data items on the group manager's computer. In this way sensitive, group activity data of any kind can be removed so that no one has access to it. In addition, this provides for removing of aberrant and un-ordinary group member activity data within the group activity data. Upon logging on to the profiler system, the group manager is then automatically provided web sites, recommendations and other information tailored to the group, as shown in block 71B.

Figure 3A:
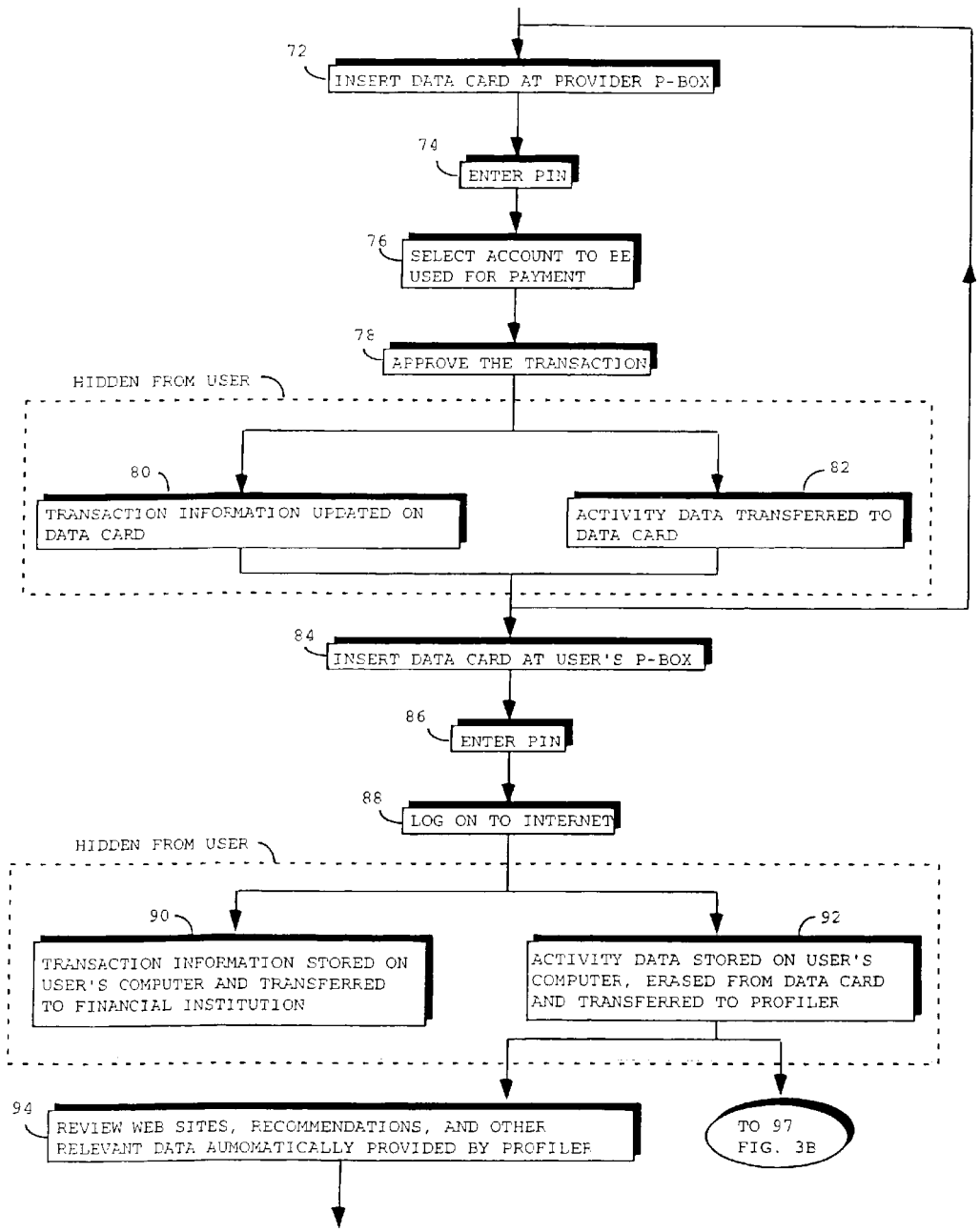
FIG. 3A illustrates the activities performed by a profiler system user in which financial transaction information and activity data are stored on a data card.

FIG. 3A illustrates the activities performed by a profiler system user in which financial transaction information and activity data are stored on a data card. In this embodiment, the data card is used to make a payment similar to a traditional transaction involving a credit card or a debit card. In this embodiment, when making any payment, the user inserts the data card at a p-box, as shown in block 72. After inserting the card, the user then authorizes access to the data card and its features by entering a PIN or performing another form of authorization, as shown in block 74. The user then is provided with a list of accounts from which to choose. Payment for the transaction will then be taken from or debited to the selected account. The list of accounts, in this embodiment, is obtained from financial data securely stored on the data card. The accounts are any accounts the user has previously selected to be accessible via the data card when setting up or editing a user profile. The accounts may be credit card accounts, bank checking accounts, bank savings accounts, money market or other accounts from any number of financial institutions or entities. The user then selects an account to be used for payment of the transaction, as shown in block 76. The user then approves the transaction, as shown in block 78, by, in one embodiment, responding to a question displayed on a screen asking the user to confirm that a specified total amount of the transaction will be drawn from the specified account.

In one embodiment, after the user approves the transaction, financial account data on the data card is updated such that information about the financial transaction is written to the data card, as shown in block 80. In addition, activity data is transferred to the data card, as shown in block 82. Updating financial account data and transferring activity data may both be hidden from the user.

After participating in some activities, the user then goes home and inserts the data card at a p-box attached to the user's computer, as shown in block 84. In this embodiment, the p-box allows for reading from and writing to the data card. The user is prompted to and authorizes access to the profiler system by entering a PIN or performing another form of authorization, as shown in block 86. The user then logs on to the profiler server via the internet, as shown in block 88. In one embodiment, upon connecting to the profiler server two things occur, both of which may be hidden from the user: (1) transaction information regarding all recent financial transactions is stored on the user's computer and transferred to the user's financial institutions via the internet, as shown in block 90; and (2) activity data is automatically uploaded from the data card and stored on the user's computer, erased from the data card, and transferred to the profiler server, as shown in block 92. In another embodiment, the user logs on to the profiler application program without connecting to the internet, and both transaction data and activity data are automatically uploaded from the data card, stored on the user's computer, and erased from the data card. In such an embodiment, at a later time, when the user logs on to the internet, the transaction data and the activity data will then be transferred to the profiler server. A benefit to erasing the activity data from the data card during uploading is added privacy and security. That is, when a user regularly transfers activity data from the data card to the user's personal computer and/or the profiler server, the activity data on the card is erased such that at any given time, there will only be a limited amount of activity data stored on the data card. This increases privacy and security such that, in the event the card is lost or stolen, only a small amount of activity data will be present on the card, namely the activity data stored since the last time the user uploaded the activity data from data card. In practice, this will typically be, at most, one day's worth of data. The user is then automatically provided web sites, recommendations and other relevant data tailored to the user, as shown in block 94.

The profiler system may also be used with groups of users. In this embodiment, the profiler system user is a member of a group. In one embodiment, a group may be a business entity such that the group members are employees and staff. In another embodiment, a group may be a collection of neighbors from a neighborhood. In yet another embodiment, the group may be a collection of relatives. In still another embodiment, the group may be a collection of businesses such that there are sub-groups of businesses. In this embodiment, the data card is used to make a payment similar to a traditional transaction involving a credit card or a debit card. In this embodiment, the group member is a user, and the processing that occurs is that same as with regard to FIG. 3A. When the user of the profiler system is a member of a group, the user may choose from one of multiple accounts, as shown in block 76. However, in one embodiment, the user first selects between personal and group accounts. In one embodiment, the choice may be between personal accounts and business or work accounts.

In one embodiment, upon connecting to the profiler server two things occur, both of which may be hidden from the user: (1) transaction information regarding all recent financial transactions is stored on the user's computer and transferred to the user's and/or group's financial institutions via the internet, as shown in block 91; and (2) activity data is automatically uploaded from the data card and stored on the user's computer, erased from the data card, and transferred to the profiler server, as shown in block 93. In this embodiment, the user's activity data is directed either or both to the user's profiler system account and/or the group's profiler system account. Such routing of the activity data may be determined by which passwords were used by the user when using the data card or in other embodiments, based on the account selected for payment of the transaction, or any other method. In this way, the data card can be used for personal and group purposes. In other embodiments, the data card may be restricted to home or group uses.

In another embodiment, the user logs on to the profiler application program without connecting to the internet, and both transaction data and activity data are automatically uploaded from the data card, stored on the user's computer, and erased from the data card. In such an embodiment, at a later time, when the user logs on to the internet, the transaction data and the activity data will then be transferred to the profiler server. A benefit to erasing the activity data from the data card during uploading is added privacy and security. That is, when a user regularly transfers activity data from the data card to the user's personal computer and/or the profiler server, the activity data on the card is erased such that at any given time, there will only be a limited amount of activity data stored on the data card. This increases privacy and security such that, in the event the card is lost or stolen, only a small amount of activity data will be present on the card, namely the activity data stored since the last time the user uploaded the activity data from data card. In practice, this will typically be, at most, one day's worth of data. The user is then automatically provided web sites, recommendations and other relevant data tailored to the user, as shown in block 94.

Figure 3B:
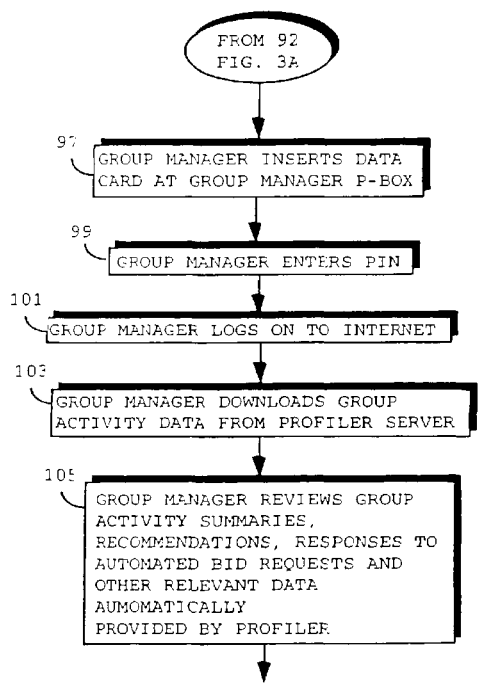
FIG. 3B illustrates the activities performed by a profiler system user and group manager in which financial transaction information and activity data are stored on a data card.

FIG. 3B illustrates the activities performed by a profiler system user and group manager in which financial transaction information and activity data are stored on a data card. In this embodiment, the profiler system user is a member of a group. When a group such as a business or non-business group is established on the profiler system, in one embodiment, a group manager or multiple group managers are designated. In such an embodiment, the group manager is given access to the group activity data, offers from suppliers to provide goods and services, recommendations and other information provided by the profiler system. Just as with regular profiler system users, the group manager, when at home or at work (or any other location) inserts the data card at a p-box attached to the group manager's computer, as shown in block 97. The group manager then authorizes access to the profiler system by entering a PIN or performing another form of authorization when logging on to the profiler server via the internet, as shown in blocks 99 and 101. In one embodiment, upon connecting to the profiler server, group activity data that has been collected by the profiler server when the group members were participating in activities is automatically downloaded to the group manager's computer, as shown in block 103. In one embodiment, group activity data is only temporarily stored on the profiler server so that only the group manager maintains a full set of activity data such that only the group manager has access to and control of the group activity data. In such an embodiment, the profiler server maintains only group habit data, group patterns, and/or the group profile. This provides added privacy to the system so that the group members and group manager do not concern themselves with what use the profiler server is making of the group activity data. In addition, in another embodiment, the group manager may select and delete activity data items on the group manager's computer. In this way, sensitive, group activity data of any kind can be removed so that no one has access to it. In addition, this provides for removing of aberrant and un-ordinary group member activity data within the group activity data. Upon logging on to the profiler system, the group manager is then automatically provided offers by providers of goods and services, recommendations and other information tailored to the group and based on the group's activity data, as shown in block 105.

C. Configuration of a Profiler System

Figure 4:
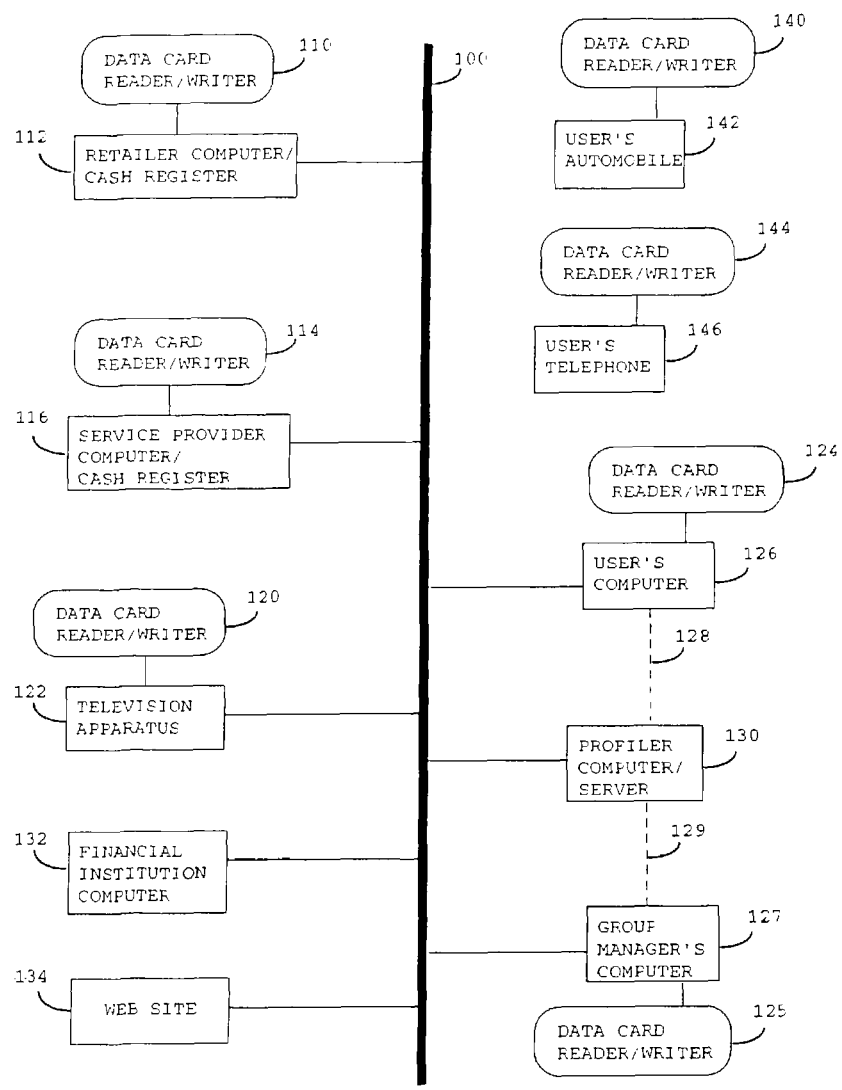
FIG. 4 illustrates various devices connected to the internet and other devices with which the profiler system is used.

FIG. 4 illustrates various devices connected to the internet and other devices with which the profiler system is used. To achieve the functionality of the profiler system described above and further described below, various devices, including p-boxes, are connected to the internet or other wide area network. In one embodiment, a data card reader/writer 110 is attached to a retailer's computer or cash register 112 which is connected to the internet 100. Similarly, a data card reader/writer 114 is attached to a service provider's computer or cash register 116 which is connected to the internet 100. A data card reader/writer 124 is attached to a user's computer which is connected to the internet. In some embodiments, a data card reader/writer 125 is attached to a group manager's computer which is connected to the internet. The profiler server 130 is likewise connected to the internet. Although only one retailer computer, one service provider computer, one user computer, one group manager computer, and one profiler server are depicted, multiple retailer computers, multiple service provider computers, multiple user computers, multiple group manager computers and multiple profiler server computers are contemplated in various embodiments. In addition, various financial institution computers 132 and web sites 134 are also connected to the internet, although only one of each are depicted.

Further, in some embodiments, the user's television apparatus 122 includes or is coupled to a data card reader/writer. The television apparatus 122 includes, but is not limited to, televisions, video disc players, video tape players, cable television boxes, satellite television boxes, etc. which are connected to the internet. In another embodiment, the user's computer 126 may connect to the profiler server 130 over dial up connection 128. In another embodiment, the group manager's computer 127 may connect to the profiler server 130 one of various connections depicted as connection 129, including, but not limited to a local area network (LAN), WAN, or dial up connection. Although not shown, in other embodiments, each of the retailer computer 112, service provider computer 116, and financial institution computer 132 may have direct leased line or dial-up connections to the profiler server 130 or one another in addition to or in place of the internet connection depicted. Moreover, the connections to the internet may be by any method known to those skilled in the art including fiber optic cable, twisted pair, infra-red, radio frequency bands, cellular phone frequency bands, or other method. Although the internet 100 is depicted, any WAN may be used.

In yet another embodiment, a data card reader/writer 140 is attached to a user's automobile 142 which may or may not be connected to the internet 100. When the user's automobile 140 does not have a connection to the internet 100 by radio transmission or other methods of transmission and communication known to those skilled in the art, various data about the user's use of the automobile is stored on the data card via data card reader/writer 140. In various embodiments, the data card reader/writer 140 may be attached to or manufactured as part of a user's automobile 142 or any other system contained in the user's automobile. In a further embodiment, a data card reader/writer 144 is attached to a user's telephone 146 which may or may not be connected to the internet 100. When the user's telephone 146 does not have a connection to the internet 100 by any method known to those skilled in the art, various data about the user's use of the user's telephone 146 is stored on the data card via data card reader/writer 144. In various embodiments, the data card reader/writer 144 may be attached to or manufactured as part of a user's telephone 146. The telephone and automobile embodiments are described in more detail hereinabove.

D. How Providers Participate in a Profiler System

Figure 5:
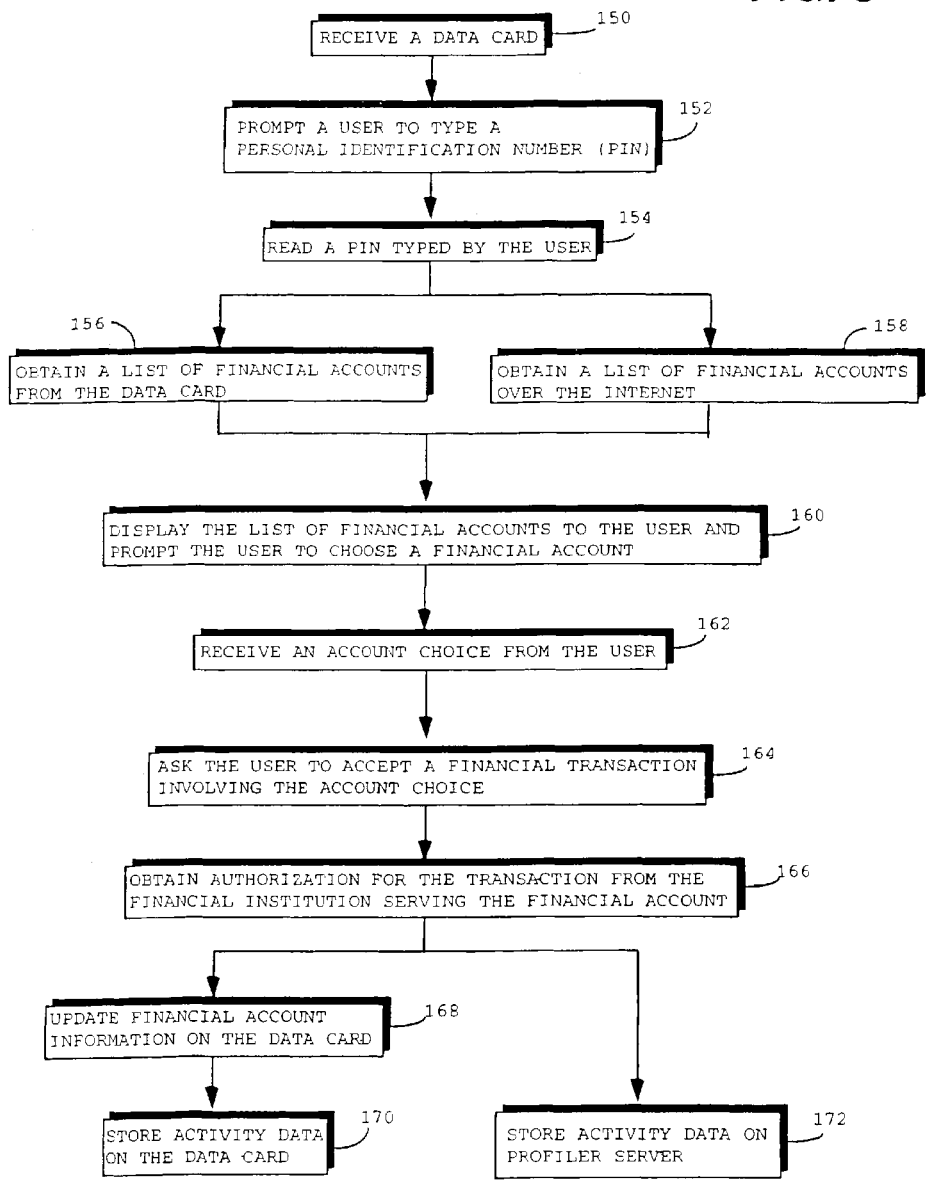
FIG. 5 illustrates the point of sale activities of a profiler system provider.

FIG. 5 illustrates the point of sale activities of a profiler system provider. As discussed above, in one embodiment, a user of the profiler system presents a data card to a provider when involved with any kind of monetary transaction. The provider may be a provider of goods or services. The provider maintains a provider system comprised of a computer or cash register including or coupled to a p-box such that the computer or cash register is connected to the internet, or other WAN. After the provider receives the data card, as shown in block 150, the provider prompts the user to authenticate use of the card and access to the profiler system such as by entering a PIN on a key pad or by any other method of authorization, as shown in block 152. In one embodiment, after reading a PIN typed by the user, as shown in block 154, authentication is achieved by comparing the PIN with an encoded number stored on the data card or on the profiler server. In another embodiment, to authenticate use of the data card, a finger print scanning device (not shown) is also coupled to the computer of the provider to scan the user's finger print and compare it with data stored either on the data card or on the profiler server. In addition, authentication may be achieved in other embodiments by any method known to those skilled in the art, including but not limited to retinal scan and voice print identification.

After authentication is completed, the provider system, in one embodiment, obtains a list of the user's financial accounts from the data card, as shown in block 156. In another embodiment, the provider system reads certain financial data from the data card and obtains a list of the user's financial accounts over the internet by communicating with the profiler server, as shown in block 158. The provider system then displays the list of financial accounts to the user and prompts the user to choose which financial account will be accessed to pay for the current transaction, as shown in block 160. The provider system receives an account choice from the user, as shown in block 162, and then asks the user to accept the financial transaction involving the account choice, as shown in block 164. More specifically, the user is asked to confirm that a certain sum representing the current transaction will be drawn from or debited from the particular account. Optionally, in one embodiment, the provider system then obtains authorization for the financial transaction from the financial institution serving or providing the financial account chosen by the user, as shown in block 166. In one embodiment, the authorization causes information concerning the transaction to be stored on the financial institution computer such that the user's account information is updated on the financial institution computer. In yet an other embodiment, after a financial institution authorizes the transaction, the user's account information may also be updated at the profiler server and/or on the data card.

Then, in one embodiment, the provider system updates financial account information on the data card, and stores activity data on the data card, as shown in blocks 168 and 170. In another embodiment, the provider system stores activity data on the profiler server, as shown in block 172. In another embodiment, the provider system asks the user whether activity data should be transferred to the profiler server and/or stored on the data card. In such an embodiment, only if the user answers affirmatively does the provider system store activity data on the profiler server and/or the data card, as shown in blocks 170 and 172. In such an embodiment, the provider system may also give the user the option to choose whether activity data should be transferred to the profiler server, the data card, or to neither.

In yet another embodiment, the data card is used only to store activity data on the data card or to cause activity data to be stored on a profiler server. In this embodiment, the data card is not used to make a payment and is swiped in addition to making payment by any traditional method. In such embodiments, the provider system receives the data card, as shown in block 150. In such an embodiment, the data card would typically be swiped by the user through a p-box coupled to the provider's computer or cash register. The provider system then prompts the user to authenticate use of the card such as by entering a PIN on a key pad or other method of authentication, as shown in block 154. In one embodiment, after reading a PIN typed by the user, as shown in block 154, authentication is achieved by comparing the PIN with an encoded number stored on the data card or on the profiler server. Optionally, in one embodiment, the provider system then obtains further authorization for use of the data card by communicating with the profiler server by any method known to those skilled in the art, including, but not limited to, internet and telephone communication. In such embodiments, the profiler server checks, for example, whether the data card is stolen or has expired, etc. The provider system then stores activity data on the data card or on the profiler server, as shown in blocks 170 and 172. In such an embodiment, all blocks after 154 and before 170 are skipped.

E. A Profiler Server

Figure 6A:
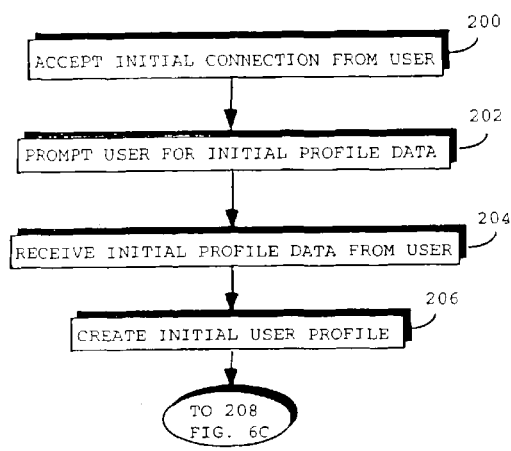
FIG. 6A illustrates the activities of a profiler system profiler server when initializing a profiler system user.

FIG. 6A illustrates the activities of a profiler system profiler server when initializing a profiler system user. In one embodiment, before a user of the profiler system uses the data card when making purchases, receiving services, or participating in activities, the user may first initialize the data card and the profiler server with user profile data. In this embodiment, the initial profile data may include, but is not limited to, name, home address, work address, basic health information, personal data, favorites, and financial data. The basic health information may include, but is not limited to, maladies and allergies regularly suffered (e.g., diabetes and sinusitis), height, weight, and physical restrictions such as a bad knee, flat feet, eyeglasses, etc. Personal data may include, but is not limited to, shirt size, pant size, physical measurements, shoe size, insurance information, etc. Favorites may include, but are not limited to, favorite brands, restaurants, flavors, colors, kinds of food, kinds of restaurants, kinds of music, musical groups, avocations, interests and hobbies. Financial data may include, but are not limited to, bank accounts and related information, credit card accounts and related information, investment accounts and related information, etc.

Referring to FIG. 6A, upon accepting an initial connection from a user, as shown in block 200, the user's data card is present in the p-box attached to or part of the user's personal computer. In this embodiment, when a user logs on for the first time, the profiler server prompts the user for data to create an initial user profile, as shown in block 202. In one embodiment, the prompting for user profile data is achieved via a sequence of internet web pages. The user supplies the requested information, the profiler server receives the user profile data, as shown in block 204, and then creates an initial internal user profile, as shown in block 206.

In another embodiment, the user profile information is requested the first time a user starts the profiler application program on a user's personal computer. In this embodiment, after the profiler application program prompts the user for the initial user profile data, the profiler application program creates an internal user profile. The profiler application program then establishes a connection with the profiler server over the internet, and provides internal user profile information to the profiler server. In yet another embodiment, requests for user profile information are staggered and presented to the user over time so as to reduce the burden and inconvenience of entering a large quantity of data when first using the profiler system. Such requests for user profile information may be made, in various embodiments, by the profiler server and/or the profiler application program. To avoid encumbering the user with the burden of entering the user profile data as described in the prior paragraphs, in another embodiment, the profiler system does not require any initial profile data to be entered by the user, and the profiler server skips steps 200 through 206.

Figure 6B:
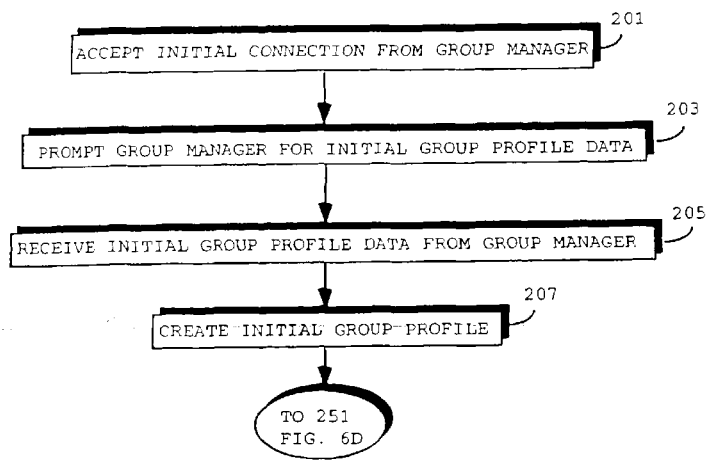
FIG. 6B illustrates the activities of a profiler system profiler server when initializing a profiler system group.

FIG. 6B illustrates the activities of a profiler system profiler server when initializing a profiler system group. In some embodiments, the user of the profiler system may be a member of a group. If so, the group manager may initialize or create the group on the profiler server. Upon accepting an initial connection from a group manager, as shown in block 201, the group manager's data card is present in the p-box attached to or part of the group manager's computer. In this embodiment, when a group manager logs on for the first time, the profiler server prompts the group manager for data to create an initial group profile, as shown in block 203. In one embodiment, the initial group profile consists of, at a minimum, a designation of all members in a group, either by name, data card number, employee number, or any other unique identifier or combination of unique identifiers. During the creation of the initial group profile, in some embodiments, it is required that the group manager enter each data card of group members into the p-box and concurrently initialize the data cards when initializing the group profile. In one embodiment, the prompting for group profile data is achieved via a sequence of internet web pages. The group manager supplies the requested information, the profiler server receives the group profile data, as shown in block 205, and then the profiler server creates an initial internal group profile, as shown in block 207.

Figure 6C:
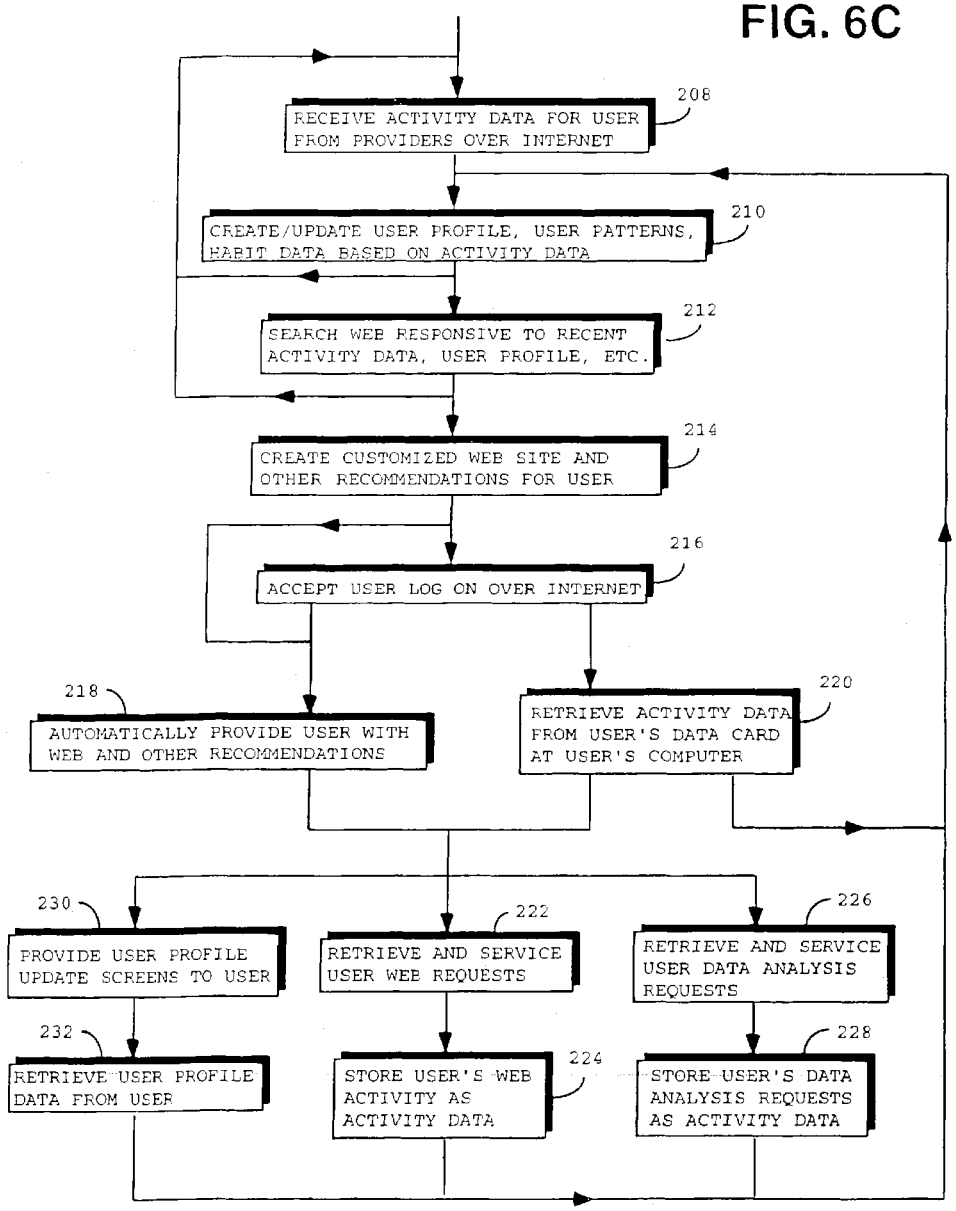
FIG. 6C illustrates the activities of a profiler system profiler server when used by a single user.

FIG. 6C illustrates the activities of a profiler system profiler server when used by a single user. When a user participates in activities using the data card, the profiler server begins receiving activity data for the user from providers over the internet, as shown in block 208. In various embodiments, when activity data is received, it is first decrypted according to methods known to those skilled in the art. In this embodiment, the profiler server begins to automatically process the activity data to create a user profile, as shown in block 210.

The profiler server continuously updates the user profile responsive to activity data received, as shown in blocks 208 and 210. That is, basic factual information is retrieved and processed by the profiler server and added to the user profile data. Such information may include, for example, maladies found at a recent doctor's visit, and brand favorites derived from recently observed buying habits as determined by evaluation of user patterns seen through the activity data. In one embodiment, information may be obtained from the activity data by inference or the execution of an inference engine. In such an embodiment, user patterns comprised of various habit data are collected and used to build a user profile. For example, if a user always purchases one brand of orange juice, that brand is entered into the user profile. Another example is, if a user always buys a particular item of clothing in one size, that size information is stored in the user profile.

Examples are numerous. Various forms of artificial intelligence, including inference engines and neural nets may be used to analyze the activity data to create the user profile, user patterns and user habit data.

The profiler server then searches the web in response to receiving the activity data and based on information contained in the user profile as shown in block 212. This automated search of the internet may be referred to as a reverse search as it is initiated by the profiler system and not by a direct request of the user. That is, the real world activities of a user are used to create user patterns which the profiler system uses to automatically issue and process searches of the internet on behalf of the user. This is the reverse of a typical web search in which a user makes a request of a computer, as here, a computer issues web requests.

More specifically, user patterns are regularly evaluated to create user habits unique to and reflective of the particular user based on the activity data. These user habits include, but are not limited to buying habits, web habits, eating habits, user health data, entertainment habits, driving habits, telephone calling habits. Based on these user habits, web queries are sent by the profiler server. The web queries may be sent to specific web sites for specific information or may be general queries sent to existing search engines. For example, certain known health-related web sites may be queried for specific health information pertinent to the user, while general queries may be sent to a search engine for new news or any information concerning a particular health topic gleaned from the activity data and/or the user profile. The processing and evaluation of activity data is ongoing. The profiler system provides rules that the profiler server uses in evaluating the activity data to create user patterns and habit data.

In addition, in one embodiment, additional intelligence is included in the profiler system to provide recommendations and information based on the user activity data, user patterns, habit data and/or user profile data. In such an embodiment, the profiler system may also provide cross-referencing of the activity data and deduced and inferred user patterns and habit data, as well as the user profile. This processing and cross-referencing may take the form of multi-processing or simultaneously executing rule engines, inference engines, or an automated agent, all of which will collectively be referred to as "bots". One such example involves a "price checking bot." In one embodiment, the "price checking bot" checks the activity data to see which products are either regularly or most often purchased, and provides suggestions to the user upon log in as to where the items can be purchased for less. A certain amount of intelligence is used so that geographically desirable stores and web stores are directed to the user. However, the stores will vary from user to user based on buying habits and the user profile. For example, the "price checking bot" may provide a local discount store to one user and an on-line store to another for the same product if the first user prefers bricks and mortar stores over internet stores. In this example, the opposite applies to the second user. In this example, the user's preferences may have been set by the user in the user profile or deduced from buying habits observed by the profiler system when analyzing the user's activity data.

Another example is a "medi-watch bot" that compares the user's health data with the user's diet. In one embodiment, the "medi-watch bot" issues warnings to the user when foods that conflict with medications or that may exacerbate a medical condition are either purchased or ordered at a restaurant.

In one embodiment, when the activity data arrives, it may be in a standard form such as a universal product code (UPC) or another code set created specially for this purpose. Various "bots" then extract, organize, and extrapolate the activity data to create user patterns and habit data, as well as to provide recommendations to the user. For example, in one embodiment, an "entertainment bot" receives an activity data specifying that the user watched a particular movie. The "entertainment bot" then looks up the movie code in a database, either on the profiler server or on the internet, and records the stars of the movie and various data about the type of movie. In one embodiment, the data for a movie that is considered important to the "entertainment bot" is what year the movie was made, whether it was a love story, a western, was a comedy, was violent, etc.

An example of the profiler system providing cross-referencing of the activity data and deducing and inferring user patterns and habit data, as well as the user profile, involves the "entertainment bot" described in the prior paragraph. The "entertainment bot" creates data that is then used by the "night out bot". Such data is used by the "night out bot" to provide recommendations about upcoming movies, plays and shows responsive to the data created by the "entertainment bot". An "eating habits bot" in conjunction with a "grocery bot" and a "restaurant bot" also provide cross-referencing, inference and deduction of and from activity data, habit data, user patterns and/or the user profile. The "eating habits bot" extracts primary ingredients from restaurant selections and grocery store purchases to determine what foods the user prefers. For example whether the user buys cheese pizza, vegetarian pizza, or pepperoni pizza (at a grocery store or restaurant) will be evaluated to determine whether the user is a vegetarian, likes plain or spicy food, likes meats, etc. In one embodiment, a "grocery bot" and a "restaurant bot" then use this information to recommend grocery store sale items and make restaurant recommendations, respectively. The number and kinds of "bots" is numerous and evolving.

After issuing web queries, the profiler server then receives, reviews, and filters the responses to the various queries and creates web site and other recommendations for the user responsive to the search results, as shown in block 214. In this way, customized web site and other recommendations are prepared for the user. Then, after authenticating the user's access to the data card and the profiler server, the profiler server accepts the user log on over the internet, as shown in block 216. Whenever a user logs into the profiler server, users are automatically provided with customized web site and other recommendations as well as other relevant information, as shown in block 218. The user then visits the recommended web sites, reads the recommendations, and reads the relevant data. In one embodiment, the profiler server keeps track of which recommendations and data are viewed and accessed by the user, and stores this as additional activity data. In another embodiment, the amount of time a user spends at various web sites, both by category or type of web site as well as by specific web site are stored as activity data and processed to create additional user patterns and web habit data which result in further recommendations.

In another embodiment, the profiler server provides the user email messages providing recommendations and relevant information based on user patterns and habit data derived and extrapolated from the user's activity data. In this embodiment, in addition to the recommendations received displayed on the user's monitor when the user logs on, the profiler server sends such email to the user at any time, and the user receives such email when checking email by any method known to those skilled in the art, such as for example, via cellular telephone or other portable computing device. In yet another embodiment, the profiler server sends by electronic page or transmission via any method known in the art, including email, a message that provides pertinent information and recommendations to the user. Such information and recommendations may include, for example, airline flight time data, an alert not to eat certain purchased food based on health data, or product recall notice information regarding items recently purchased.

In another embodiment, upon the user logging on, the profiler server retrieves activity data from the user's data card which is inserted in the user's computer, or a p-box coupled to the user's computer, as shown in block 220. In such embodiments, activity data stored on the data card is transferred to the profiler server and evaluated, as shown in block 210. In various embodiments, the activity data is received by the profiler server over the internet, or by direct connection of any kind known in the art, from the user's p-box or user's computer. In various embodiments, when activity data is received, it is first decrypted according to methods known to those skilled in the art. This encryption make take place on both the user's computer and on the profiler server. In one embodiment, the activity data is transferred from the data card and decrypted on the user's computer, stored on the user's computer, and then encrypted and transferred to the profiler server which then decrypts the activity data for processing. In yet another embodiment, when activity data is stored on the user's computer, it remains in encrypted form to prevent access to it by others than the intended user. In such an embodiment, the profiler application program or other components of the profiler system decrypt activity data only when being accessed by a profiler application program after a user has entered a data card and authorized use of the data card and the profiler system.

In one embodiment, the profiler server retrieves and services user web requests, as shown in block 222. Upon receiving a web request, the profiler server combines the request with pertinent stored information such as the user profile and user patterns including user habits to send better directed, more focused and more effective web queries. In addition, the profiler server filters the web responses and provides only the most relevant and pertinent search results to the user based on evaluating the responses against the user's web request, the user profile data, and user patterns including user habits. Just as other activity data is transmitted to the profiler server, in one embodiment, the user's web activities are stored by the profiler server as activity data, as shown in block 224. Web activity may include user web requests made by the user as well as all web sites visited by the user, the amount of time spent visiting particular web sites, etc.

To allow for additional privacy, in one embodiment, the user is provided the opportunity to turn off the automatic monitoring of web viewing and creation of activity data resulting from web viewing. This feature may be implemented according to any methods known to those skilled in the art, including, but not limited to, an on-screen button or pull-down menu item. In addition in any such embodiments, whether automated monitoring of web viewing is on or off is reflected graphically on the screen according to methods known to those skilled in the art. For example, in one embodiment, a small graphic commonly referred to as an icon may change color or change image depending on whether automatic web activity monitoring is selected by the user to be on or off.

In another embodiment, the profiler server provides various personal analysis programs that a user can execute to evaluate the user's buying and other habits, as well as financial and other data. In one embodiment, the personal analysis programs are run on the profiler server and evaluate data stored on the profiler server. In another embodiment, the personal analysis programs are special purpose mini-application programs, such as JAVA applets, that are provided by the profiler server and downloaded when the user requests a particular personal analysis program. In this embodiment, the personal analysis programs may access either or both data stored on the user's computer or on the profiler server. With regard to any of these embodiments, the profiler server retrieves and services the user's data analysis requests, as shown in block 226. As with any other activities engaged in by the user, the requests for data analysis create activity data that is stored by the profiler server, as shown in block 228.

The profiler system also allows the user to update the user profile data at any time after providing initial user profile data or after profile data is created by the profiler server. In one embodiment, when the user is logged onto the profiler server, the user pulls down a menu and chooses "update user profile." In an other embodiment, the user clicks on an "update user profile" button provided on the screen. In response to receiving the request to update user profile data, in one such embodiment, the profiler server provides user profile update screens to the user, as shown in block 230. After providing the user profile update screen to the user, the profiler server retrieves updated user profile data provided by the user, as shown in block 232. In another embodiment, the profiler application program services the user's request to update user profile data and updates the profiler application program's internal user profile data. In this embodiment, the profiler application program then transmits updated user profile data to the profiler server.

FIG. 6D illustrates the activities of a profiler system profiler server when used by a group and a group manager. When a group member participates in activities using the data card, the profiler server begins receiving activity data for the user from providers over the internet, as shown in block 251. The activity data is then routed to the appropriate group and/or user accounts depending on whether the data is group activity data, user activity data, or both. Group activity data may be an aggregation of user activity data. As the processing that occurs when a single user uses the profiler system is already described with regard to FIG. 6C, the following discussion focuses only where group processing and group features of the profiler server may differ, even though group processing may be simultaneous with single user processing in some embodiments.

In one embodiment, the profiler server begins to automatically process the activity data to create a group profile, as shown in block 253. The profiler server continuously updates the group profile responsive to activity data received, as shown in blocks 251 and 253. That is, basic factual information is retrieved and processed by the profiler server and added to the group profile data. When used for non-business group purposes, such information may include, for example, brand and item trends, and favorite retailers and providers derived from recently observed buying habits as determined by evaluation of user patterns seen through the activity data. When used for business purposes, such information may include, for example, recent employee travel data and recent employee purchase data, including derivation of brand, retailer and provider favorites gleaned from the group member patterns culled from group activity data. In one embodiment, information may be obtained from the activity data by inference or the execution of an inference engine. Various forms of artificial intelligence, including inference engines and neural nets may be used to analyze the activity data to create and grow the group profile, group patterns and group habit data In one embodiment, user patterns comprised of various group habit data are collected and used to build a group profile. For example, if a group regularly always purchases one brand of copy paper or toilet paper, that brand is entered into the group profile. Another example is, if a group always buys a particular item in one size, that size information is stored in the group profile entry for that item. Examples are numerous.

In another embodiment in which the group is a group of businesses, group patterns comprised of various habit data are collected and used to build a group profile. For example, if a group regularly purchases one brand or kind of a particular item, such as a stapler or copy machine paper, that brand and/or kind of item is entered into the group profile. Another example is, if a group always buys a particular item at particular time intervals or at a particular time of year or time of the month, such buying trends are learned and stored as group patterns, group habit data and/or in the group profile. Other examples are numerous.

The profiler server then searches the web in response to receiving the group activity data and based on information contained in the group profile as shown in block 255. More specifically, group patterns are regularly evaluated to create group habits unique to and reflective of the particular group based on the group activity data. Group habits may include, but are not limited to buying habits, web habits, restaurant habits, entertainment habits, driving habits, telephone calling habits. Based on these group habits, web queries are sent by the profiler server. The web queries may be sent to specific web sites for specific information or may be general queries sent to existing search engines. For example, certain known travel web sites may be queried for specific travel information pertinent to the group, such as derived from regular flight to San Jose airport the first Tuesday of every month. General queries may be sent to a search engine for new news or any information concerning a particular topic gleaned from the group activity data and/or the group profile. Such information may be, for example, tax related news stories for a group which happens to be an accounting firm which the profiler system to have an accounting interest based on analysis of group activity data such as group member web research activity data, or explicit statement of the group's business or purpose in the group profile. The processing and evaluation of activity data is ongoing. The profiler system provides rules that the profiler server uses in evaluating the group activity data to create group patterns and group habit data.

In addition, in one embodiment, additional intelligence is included in the profiler system to provide recommendations and information based on the group activity data, group patterns, group habit data and/or group profile data. In such an embodiment, the profiler system may also provide cross-referencing of the group activity data and deduced and inferred group patterns and group habit data, as well as the group profile. This processing and cross-referencing may take the form of multi-processing or simultaneously executing rule engines, inference engines, or an automated agent, all of which will collectively be referred to as "bots". One such example involves a "price checking bot" that works hand in hand with a "goods purchased bot." In one embodiment, the "goods purchased bot" examines group activity data to learn which products are either regularly or most often purchased by the group. Based on information provided by the "goods purchased bot," the "price checking bot" sends web queries to learn the prices of the goods at various provider's web sites. The "price checking bot" then receives and processes responses to the queries, and provides suggestions to the group manager upon log in as to where the items can be purchased for less or for a group or bulk discount. A certain amount of intelligence is used so that geographically desirable stores as well as web stores may be reported to the group manager. However, the stores will vary from group to group based on buying habits and the group profile. For example, the "price checking bot" may provide a local discount store to one group and an on-line store to another for the same product if the first group prefers bricks and mortar stores over internet stores. In this example, the group's preferences may have been set by the group in the group profile or deduced from buying habits observed by the profiler system when analyzing the group activity data.

Various "bots" then extract, organize, and extrapolate the group activity data to create group patterns and group habit data, as well as to provide recommendations to the group. For example, in one embodiment, a "travel bot" may determine flying habits such as regular trips or preferred airlines.

In yet another embodiment, the profiler system also issues automatic requests for bids based on past group activity data, group patterns and the group profile. That is, using the example discussed above, if the "travel bot" determines that one or more members of a group regularly flies to San Jose airport on the first Tuesday of every month, a "request for bid" bot may take this information and send to known travel agent or airline web sites requesting a bid for a group of flights in an attempt to achieve a multiple purchase discount.

Similarly, the "request for bid bot" goes beyond what the "price checking bot" does. Based on the group activity data, group patterns and the group profile, and information provided by the "goods purchased bot", a "request for bid bot" may organize office supplies regularly purchased into a group and automatically send a request for bid for monthly or quarterly delivery of the group's office supplies to internet and local office supply stores. In this way, a buying cooperative comprised of businesses or groups of persons may achieve bulk and/or regular purchase discounts. In this way, the "request for bid bot" serves as an automated business to business reverse bidding mechanism. In one embodiment, such automatic request for bids may be turned off or specified to run as to only certain goods or services by the group manager. The number and kinds of "bots" is numerous and evolving.

In another embodiment, in the business to business context, selling activity and inventory are stored as activity data. In such an embodiment, a "selling activity bot" keeps track of goods sold by one company, and an "inventory watch bot" provides recommendations to the group manager of the company responsive to information obtained from the company's activity data and the "selling activity bot." For example, in one embodiment, when the "inventory watch bot" learns that there is an oversupply of a particular good, the "inventory watch bot" may query the "selling activity bot" and prepare a recommendation to the group manager to offer a particular quantity of the overstocked item to a regular purchaser at a discount. In another embodiment, the "inventory watch bot" may automatically send offers to regular purchasers informing them of a sale on the item when the "inventory watch bot" deduces that there is an overstocked item. In such an embodiment, the group manager may also be informed by the profiler system that the offers have been sent.

In a related embodiment, the "inventory watch bot" may determine that stock on an item is too low to meet anticipated demand as determined by automatic analysis of prior selling activity data. In such a situation, the "inventory watch bot" may recommend to the group manager to increase production of the particular item to meet anticipated demand of the item. In another embodiment, the "inventory watch bot" may automatically send mail to the company's factory requesting an increase in production of the particular item while concurrently informing the group manager that such a request has been sent. In these embodiments, inventory activity data may be acquired by an employee scanning bar coded, boxes, crates, pallets or containers of goods while a data card is inserted in a scanner or inserted in a computing device to which the scanner transmits. In another embodiment, inventory data may be obtained directly from a manufacturing facility in a similar manner. In these embodiments, selling activity data may be obtained using a data card while an employee processes orders such that each order entered by a particular employee is stored by the profiler system as selling activity data. In an alternative embodiment, such selling activity data may be obtained from a database of filled invoices, purchase orders or the like.

After issuing web queries, including requests for bids, the profiler server then receives, reviews, and filters the responses to the various queries and requests, and creates recommendations for the group manager responsive to the results, as shown in block 257. In this way, customized recommendations are prepared for the group manager. Then, after authenticating the group manager's access to the data card and the profiler server, the profiler server accepts the group manager log on over the internet, as shown in block 259. Whenever a group manager logs into the profiler server, group manager's are automatically provided with customized recommendations as well as other relevant information, as shown in block 261. The group manager then visits recommended web sites, reads the recommendations, and reads other the relevant data. In one embodiment, the profiler server keeps track of which recommendations and data are viewed and accessed by the group manager, and stores this as additional activity data. In another embodiment, the amount of time group members spend at various web sites, both by category or type of web site as well as by specific web site are stored as group activity data and processed to create additional group patterns and group web habit data which result in further recommendations.

In another embodiment, upon the group manager logging on, the profiler server transfers group activity data from the profiler server to the group manager's computer, as shown in block 263. In various embodiments, the group activity data is transferred by the profiler server over the internet, or by direct connection of any kind known in the art, to the group manager's computer. In various embodiments, when activity data is received, it is first decrypted according to methods known to those skilled in the art. This encryption make take place on both the user's computer and on the profiler server. In yet another embodiment, when group activity data is stored on the group manager's computer, it remains in encrypted form to prevent access to it by others than the group manager. In such an embodiment, the profiler application program or other components of the profiler system decrypt group activity data only when being accessed by a profiler application program after a group manager has entered a data card and authorized use of the data card and the profiler system.

In another embodiment, the profiler server provides various group analysis programs that a program manager can execute to evaluate the group's buying and other habits. In one embodiment, the group analysis programs are run on the profiler server and evaluate data stored on the profiler server. In another embodiment, the group analysis programs are special purpose mini-application programs, such as JAVA applets, that are provided by the profiler server and downloaded when the group manager requests a particular personal analysis program. In this embodiment, the personal analysis programs may access either or both data stored on the group manager's computer or on the profiler server. With regard to any of these embodiments, the profiler server retrieves and services the user's data analysis requests, as shown in block 265.

The profiler system also allows the group manager to update the group profile data at any time after providing initial group profile data. In one embodiment, when the group manager is logged onto the profiler server, the group manager pulls down a menu and chooses "update group profile." In another embodiment, the group manager clicks on an "update group profile" button provided on the screen. In response to receiving the request to update group profile data, in one such embodiment, the profiler server provides group profile update screens to the group manager, as shown in block 267. After providing the user profile update screen to the user, the profiler server retrieves updated group profile data provided by the group manager, as shown in block 269. In another embodiment, the profiler application program services the program manager's request to update group profile data and updates the profiler application program's internal group profile data. In this embodiment, the profiler application program then transmits updated group profile data to the profiler server.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense. Therefore, the scope of the invention should be limited only by the appended claims.

What is claimed is:

1. A method comprising:
   recording activity data by a portable user device on a transportable recordable medium (TRM) coupled to the user device, the recording being in response to user participation in an activity;
   transferring the activity data by the user device to a profiler across a network, the profiler storing a user controlled profile including the activity data;
   displaying the activity data and user selectable options for the user controlled profile through the user device; and
   initiating a monetary transaction through the user device based on one of the plurality of recommendations; and
   receiving a plurality of recommendations for a user at the user device inferred from the activity data by a user selected profiling program.

2. The method of claim 1 further comprising:
   sliding the TRM through a TRM reader when paying for goods, services, and entertainment.

3. The method of claim 2 wherein transferring comprises:
   transferring the activity data over the network to the profiler responsive to sliding.

4. The method of claim 2 further comprising:
   recording the activity data on the TRM via a TRM reader/writer when paying for goods, services, and entertainment.

5. The method of claim 4 wherein transferring comprises:
   transferring the activity data from a TRM over the network to the profiler via a personal computing device.

6. The method of claim 5, wherein the personal computing device is a cellular phone.

7. The method of claim 4 further comprising:
   recording the activity data on the TRM via a TRM reader/writer when watching television, paying for transportation, placing telephone calls, and driving a vehicle.

8. The method of claim 2 further comprising:
sliding the TRM through a TRM reader when doing at least one of the following: watching television, paying for transportation, placing telephone calls, or driving a vehicle.

9. The method of claim 1 further comprising:
invoking a monetary transaction;
presenting the TRM when a payment is requested;
authenticating access rights to the TRM;
selecting an account derived from a financial data on the TRM; and
consenting to the monetary transaction.

10. The method of claim 9 wherein selecting the account comprises:
choosing among accounts from at least two different financial entities.

11. The method of claim 10 wherein authenticating comprises:
entering a personal identification number (PIN) into the user device.

12. The method of claim 9, wherein the user controlled profile has security and access settings controlled by a user.

13. The method of claim 1, wherein the activity data is a universal product code (UPC).

14. The method of claim 1, wherein the plurality of recommendations include alternate locations for purchasing an item.

15. The method of claim 14, further comprising:
displaying alternate locations that are geographically relevant to a user.

16. The method of claim 14, wherein the alternate locations are determined based on user preferences.

17. The method of claim 1, further comprising:
receiving the activity data through scanning of a bar code.

18. The method of claim 1, wherein the plurality of recommendations include a comparison of prices for an item at local stores.

19. The method of claim 1, wherein the plurality of recommendations include a price for an item at an on-line store.

20. The method of claim 19, further comprising:
providing an interface to initiate purchase of the item through the user device.

21. The method of claim 1, wherein the activity data is transferred to the profiler to generate a web query.

22. The method of claim 1 wherein the activity data is recorded on the TRM by the user device, and wherein the plurality of recommendations are displayed by the user device.

23. The method of claim 22, wherein the user device is any one of a cellular telephone, a portable computer, an electronic personal organizer, desktop computer or dedicated Internet device.

24. The method of claim 1, wherein the user selected profiling program is any one of a bot, an inference engine or a neural network.

25. A computer-readable medium having instructions stored therein, which when executed cause a computer to perform a set of operations comprising:
recording activity data by a portable user device on a transportable recordable medium (TRM) coupled to the user device, the recording being in response to user participation in an activity;
transferring the activity data at the user device to a profiler across a network, the profiler storing a user controlled profile including the activity data;
displaying the activity data and user selectable options for the user controlled profile through the user device; and
initiating a monetary transaction through the user device based on one of the plurality of recommendations; and
receiving a plurality of recommendations by the user device inferred from the activity data by a user selected profiling program.

26. The computer-readable medium of claim 25 further comprising:
sliding the TRM through a TRM reader when paying for goods, services, and entertainment.

27. The computer-readable medium of claim 26 wherein transferring comprises:
transferring the activity data over the network to the profiler responsive to sliding.

28. The computer-readable medium of claim 26 having further instructions stored therein which when executed cause the computer to perform a further set of operations comprising:
recording the activity data on the TRM via a TRM reader/writer when paying for goods, services, and entertainment.

29. The computer-readable medium of claim 28 wherein transferring comprises:
transferring the activity data from a TRM over the network to the profiler via a personal computing device.

30. The computer-readable medium of claim 29, wherein the personal computing device is a cellular phone.

31. The computer-readable medium of claim 28 having further instructions stored therein which when executed cause the computer to perform a further set of operations comprising:
recording the activity data on the TRM via a TRM reader/writer when watching television, paying for transportation, placing telephone calls, and driving a vehicle.

32. The computer-readable medium of claim 26 having further instructions stored therein which when executed cause the computer to perform a further set of operations comprising:
sliding the TRM through a TRM reader when doing at least one of the following: watching television, paying for transportation, placing telephone calls, or driving a vehicle.

33. The computer-readable medium of claim 25 having further instructions stored therein which when executed cause the computer to perform a further set of operations comprising:
invoking a monetary transaction;
presenting the TRM when a payment is requested;
authenticating access rights to the TRM;
selecting an account derived from a financial data on the TRM; and
consenting to the monetary transaction.

34. The computer-readable medium of claim 33 wherein selecting the account comprises:
choosing among accounts from at least two different financial entities.

35. The computer-readable medium of claim 34 wherein authenticating comprises:
entering a personal identification number (PIN) into the user device.

36. The computer-readable medium of claim 33, wherein the user controlled profile has security and access settings controlled by a user.

37. The computer-readable medium of claim 25, wherein the activity data is a universal product code (UPC).

38. The computer-readable medium of claim 25, wherein the plurality of recommendations include alternate locations for purchasing an item.

39. The computer-readable medium of claim 38, having further instructions stored therein which when executed cause the computer to perform a further set of operations comprising:
displaying alternate locations that are geographically relevant to a user.

40. The computer-readable medium of claim 38, wherein the alternate locations are determined based on user preferences.

41. The computer-readable medium of claim 25, having further instructions stored therein which when executed cause the computer to perform a further set of operations comprising:
receiving the activity data through scanning of a bar code.

42. The computer-readable medium of claim 25, wherein the plurality of recommendations include a comparison of prices for an item at local stores.

43. The computer-readable medium of claim 25, wherein the plurality of recommendations include a price for an item at an on-line store.

44. The computer-readable medium of claim 43, having further instructions stored therein which when executed cause the computer to perform a further set of operations comprising:
providing an interface to initiate purchase of the item through the user device.

45. The computer-readable medium of claim 25, wherein the activity data is transferred to the profiler to generate a web query.

46. The computer-readable medium of claim 25, wherein activity data is recorded on the TRM by the user device, and wherein the plurality of recommendations are displayed by the user device.

47. The computer-readable medium of claim 46, wherein the user device is any one of a cellular telephone, a portable computer, an electronic personal organizer, desktop computer or dedicated Internet device.

48. The computer-readable medium of claim 25, wherein the user selected profiling program is any one of a bot, an inference engine or a neural network.

* * * * *